(12) United States Patent
Goldberg et al.

(10) Patent No.: US 10,299,828 B2
(45) Date of Patent: May 28, 2019

(54) ANCHOR DELIVERY SYSTEM AND METHOD

(71) Applicant: Escala Medical Ltd., Misgav (IL)

(72) Inventors: Roger P. Goldberg, Evanston, IL (US); Douglas S. Scherr, Scarsdale, NY (US)

(73) Assignee: ESCALA MEDICAL LTD., Misgav (IL)

( * ) Notice: Subject to any disclaimer, the term of this patent is extended or adjusted under 35 U.S.C. 154(b) by 403 days.

(21) Appl. No.: 14/909,121

(22) PCT Filed: Aug. 4, 2014

(86) PCT No.: PCT/IB2014/063677
§ 371 (c)(1),
(2) Date: Jan. 31, 2016

(87) PCT Pub. No.: WO2015/015475
PCT Pub. Date: Feb. 5, 2015

(65) Prior Publication Data
US 2016/0235440 A1  Aug. 18, 2016

Related U.S. Application Data

(60) Provisional application No. 61/861,920, filed on Aug. 2, 2013.

(51) Int. Cl.
*A61F 2/00* (2006.01)
*A61B 17/42* (2006.01)
(Continued)

(52) U.S. Cl.
CPC ...... *A61B 17/3468* (2013.01); *A61B 17/0401* (2013.01); *A61B 17/0487* (2013.01); *A61B 17/3478* (2013.01); *A61B 17/42* (2013.01); *A61B 17/3417* (2013.01); *A61B 2017/0065* (2013.01); *A61B 2017/00805* (2013.01); *A61B 2017/0409* (2013.01); *A61B 2017/0417* (2013.01); *A61B 2017/0458* (2013.01); *A61B 2017/0464* (2013.01); *A61B 2217/007* (2013.01); *A61F 2002/0072* (2013.01)

(58) Field of Classification Search
CPC . A61B 17/3468; A61B 17/42; A61B 17/0487; A61B 17/0401; A61B 2017/00805; A61B 2017/0409; A61B 2017/0417; A61F 2/00–0063
See application file for complete search history.

(56) References Cited

U.S. PATENT DOCUMENTS 6,071,292 A   6/2000 Makower et al.
6,981,983 B1  1/2006 Rosenblatt et al.
(Continued)

FOREIGN PATENT DOCUMENTS

WO   2005086885 A2   9/2005

*Primary Examiner* — Thaddeus B Cox
(74) *Attorney, Agent, or Firm* — The Roy Gross Law Firm, LLC; Roy Gross

(57) ABSTRACT

A system for incisionless transvaginal sacrospinous ligament fixation, the system including an anchoring unit configured to affix a vaginal wall to a sacrospinous ligament; and a piercing tip configured to: pierce said vaginal wall, pierce said sacrospinous ligament, and deploy a first portion of said anchoring unit though said pierced vaginal wall and said pierced sacrospinous ligament, thereby disposing said first portion at said sacrospinous ligament.

11 Claims, 28 Drawing Sheets

(51) Int. Cl.
*A61B 17/04* (2006.01)
*A61B 17/34* (2006.01)
*A61B 17/00* (2006.01)

(56) References Cited

U.S. PATENT DOCUMENTS

| | | |
|---|---|---|
| 7,338,502 B2 | 3/2008 | Rosenblatt |
| 2004/0044329 A1 | 3/2004 | Trudell |
| 2004/0147958 A1 | 7/2004 | Lam et al. |
| 2005/0203550 A1 | 9/2005 | Laufer et al. |
| 2006/0265042 A1 | 11/2006 | Catanese, III et al. |
| 2006/0276871 A1 | 12/2006 | Lamson et al. |
| 2010/0010508 A1 | 1/2010 | Takahashi et al. |
| 2012/0316384 A1 | 12/2012 | Arnold |
| 2013/0023724 A1 | 1/2013 | Allen et al. |
| 2013/0109910 A1 | 5/2013 | Alexander et al. |

| EMBODIMENT NUMBER | PICTURE |
|---|---|
| Embodiment- 01 |  |
| Embodiment- 02 |  |
| Embodiment - 03 |  |
| Embodiment - 04 |  |
| Embodiment - 05 |  |
| Embodiment - 06 |  |

ANCHOR DELIVERY SYSTEM AND METHOD

CROSS REFERENCE TO RELATED APPLICATIONS

This application claims the benefit of U.S. Provisional Patent Application No. 61/861,920, filed Aug. 2, 2013 and entitled "Anchor Delivery System and Method", which is incorporated herein by reference in its entirety.

FIELD OF THE INVENTION

The invention relates to the field of organ prolapse repair.

BACKGROUND

There are a variety of medical devices and procedures used for supporting portions of a patient's body such as for treating pelvic organ prolapse. The pelvic floor of a patient includes muscles and ligaments that support organs, such as the bladder, colon, urethra, uterus, cervix, small intestine, or rectum within a pelvic cavity. Pelvic organ prolapse occurs when this normal structural support stretches or weakens, causing the descent or droop of the organs. There are four main forms of pelvic organ prolapse. Cystocele is a weakening of the vaginal wall causing the bladder to protrude into the vagina. Rectocele is a weakening of the back wall of the vagina causing the rectum to protrude into the vagina. In vaginal vault prolapse (uterine prolapse) the uterus intrudes into the vagina from above, and in enterocele the small intestine descends and protrudes into the vagina.

One procedure for treating this type of disorder comprises securing the apex of the vagina to a sacrospinous ligament or other structurally supportive tissue within the pelvic region. In a majority of circumstances, anterior and posterior prolapses are directly caused by apical support defects. By supporting the vaginal apex region, most of the apically related prolapses of the vaginal area are relieved.

Many conventional prolapse treatment procedures require an incision such as an open abdominal approach. In particular, these procedures include placing a mesh, graft, or other implant within the pelvic region of a patient. The mesh, graft, or other implant is delivered to the pelvic region through one or more vaginal incisions and/or through exterior incisions of the patient. Thus, this requires substantial surgery where a patient can be typically hospitalized for days after the surgery as part of their recovery.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

Accordingly, a system and method for performing incision-less repairs of a prolapse in the pelvic region are highly desirable. The present invention provides a needle-based fixation solution combined with an optional soft tissue bonding agent. The present invention enables prolapse repair without surgical incision. Thus, the present invention eliminates the need for hospitalization post-surgery and general anesthesia during surgery. The present invention is directed toward further solutions to address these needs, in addition to having other desirable characteristics.

In accordance with an embodiment of the present invention an incisionless transvaginal sacrospinous ligament fixation system has an anchoring unit configured to affix a vaginal wall to a sacrospinous ligament, a piercing tip that is configured to pierce the vaginal wall, at least partially pierce the sacrospinous ligament, and deploy a first portion of the anchoring unit through the pierced vaginal wall and the at least partially pierced sacrospinous ligament, thereby disposing the first portion at the sacrospinous ligament.

In accordance with aspects of the present invention, the piercing tip is further comprised to deploy a second portion of the anchoring unit through the at least partially pierced sacrospinous ligament and through the pierced vaginal wall, wherein the second portion is disposed at an apex region of the vaginal wall, thereby affixing the vaginal wall to the sacrospinous ligament.

In accordance with aspects of the present invention, the second portion is a suture that is configured to fasten to the apex region of the vaginal wall via a fastening mechanism.

In accordance with aspects of the present invention, the first portion of the anchoring unit comprises a collapsible anchoring mechanism and the second portion of the anchoring mechanism comprises a stopper.

In accordance with aspects of the present invention, the piercing tip is further configured with a delivery port for delivering a therapeutic substance.

In accordance with aspects of the present invention, the system further comprises a first arm configured with a first anchoring unit and a first piercing tip, a second arm configured with a second anchoring unit and a second piercing tip, wherein the first arm and the second arm are further configured to grasp a portion of the vaginal wall that is positioned against the sacrospinous ligament, thereby surrounding the sacrospinous ligament.

In accordance with aspects of the present invention, a suture is configured with both of the first anchoring unit and the second anchoring unit, wherein the first piercing tip is configured to deploy the suture through the first piercings of the sacrospinous ligament and the vaginal wall, and wherein the second piercing tip is further configured to deploy the suture through the second piercings of the sacrospinous ligament and the vaginal wall, and wherein the suture is disposed at an apex region of the vaginal wall, thereby affixing the vaginal wall to the sacrospinous ligament.

In accordance with aspects of the present invention, a method for incisionless transvaginal sacrospinous ligament fixation includes piercing a vaginal wall, at least partially piercing a sacrospinous ligament, deploying a first portion of an anchoring unit through the pierced vaginal wall and the at least partially pierced sacrospinous ligament, thereby disposing the first portion at the sacrospinous ligament.

In accordance with aspects of the present invention, the method further comprises deploying a second portion of the anchoring unit through the at least partially pierced sacrospinous ligament and through the pierced vaginal wall, wherein the second portion is disposed at an apex region of the vaginal wall, thereby affixing the vaginal wall to the sacrospinous ligament.

In accordance with aspects of the present invention, the method further comprises deploying the second portion wherein the second portion is a suture that is configured to fasten to the apex region of the vaginal wall via a fastening mechanism.

In accordance with aspects of the present invention, the method further comprises deploying the first portion wherein the first anchoring unit comprises a collapsible anchoring mechanism, and wherein deploying the second portion wherein the second portion comprises a stopper.

In accordance with aspects of the present invention, the method further comprises delivering a therapeutic substance.

In accordance with aspects of the present invention, the method further comprises grasping, via a first arm and a second arm, a portion of the vaginal wall that is positioned against the sacrospinous ligament, thereby surrounding the sacrospinous ligament, performing the piercing and deploying steps via the first arm, thereby affixing the vaginal wall to the sacrospinous ligament at a first location; and performing the piercing and deploying steps via the second arm, thereby affixing the vaginal wall to the sacrospinous ligament at a second location.

In accordance with aspects of the present invention, the method further comprises deploying the second portion wherein the second portion is a suture that is disposed at the first and the second locations, and at an apex region of the vaginal wall, thereby affixing the vaginal wall to the sacrospinous ligament.

In accordance with an embodiment of the present invention, an anchor delivery system has a delivery conduit having a wall forming an interior lumen, a first end, and a second end. The second end terminates with a delivery aperture. The anchor delivery system has an elongate cannula having a wall sized, dimensioned, and configured for slidable disposal within and along the interior lumen of the delivery conduit. The elongate cannula has an interior lumen, a first end, and a second end. The second end terminates with a tissue piercing tip and aperture. The anchor delivery system has one or more delivery ports disposed through the wall of the elongate cannula and proximal to the tissue piercing tip and aperture. The anchor delivery system has a pushrod sized, dimensioned, and configured for slidable disposal within and along the interior lumen of the elongate cannula. The anchor delivery system has a supply port into the interior lumen of the elongate cannula. The anchor delivery system has at least one anchor coupled with a suture. The anchor and suture are sized, dimensioned, and configured for slidable disposal within and along the interior lumen of the elongate cannula. The suture has a first end coupled to the anchor and a second end forming a loose tail. The anchor delivery system is arranged in such a way that the anchor and suture are disposed within the interior lumen of the elongate cannula. The elongate cannula is disposed within the interior lumen of the delivery conduit, and the pushrod is disposed within the interior lumen of the elongate cannula between the anchor and the first end of the elongate cannula. A push force applied to the pushrod causes the pushrod to slide through and push the anchor through and out the tissue piercing tip of the elongate cannula for implantation into tissue.

In accordance with aspects of the present invention, the system further optionally includes a liquid or gel supplied to the interior lumen of the elongate cannula through the supply port. Upon removal of the pushrod from the interior lumen of the elongate cannula, the liquid or gel can exit the interior lumen of the elongate cannula through the one or more delivery ports and the tissue piercing tip and aperture. In one aspect, the liquid or gel is an adhesive. In a further aspect, the adhesive is bioglue. In another aspect, the liquid or gel is an agent that increases tissue ingrowth/inflammation.

In accordance with aspects of the present invention, the pushrod is laterally flexible and axially rigid. In another aspect, the pushrod includes a handle. A push force is applied to the handle of the pushrod causing the pushrod to slide through and push the anchor through and out the tissue piercing tip and aperture of the elongate cannula for implantation into tissue.

In accordance with aspects of the present invention, the supply port can be disposed through the wall of the elongate cannula into the interior lumen of the elongate cannula at a location distal from the tissue piercing tip and aperture. In accordance with aspects of the present invention, the one or more delivery ports can be positioned about 2 centimeters from each other along the wall of the elongate cannula.

In accordance with aspects of the present invention, the anchor is bioabsorbable. In some aspects, the anchor coupled with the suture forms a T-shape when the anchor is implanted into tissue. In another aspect, the suture includes a plurality of barbs.

In accordance with aspects of the present invention, a maximum distance between the first end of the delivery conduit and the first end of elongate cannula is between about 0.5 centimeters and about 1.5 centimeters. In accordance with an embodiment of the present invention, an anchor delivery system kit has a delivery conduit having a wall forming an interior lumen, a first end, and a second end. The second end terminates with a delivery aperture. The anchor delivery system kit has an elongate cannula having a wall sized, dimensioned, and configured for slidable disposal within and along the interior lumen of the delivery conduit. The elongate cannula has an interior lumen, a first end, and a second end. The second end terminates with a tissue piercing tip and aperture. The anchor delivery system kit has one or more delivery ports disposed through the wall of the elongate cannula and proximal to the tissue piercing tip and aperture. The anchor delivery system kit has a pushrod sized, dimensioned, and configured for slidable disposal within and along the interior lumen of the elongate cannula. The anchor delivery system kit has a supply port into the interior lumen of the elongate cannula. The anchor delivery system kit has at least one anchor coupled with a suture. The anchor and suture sized, dimensioned, and configured for slidable disposal within and along the interior lumen of the elongate cannula. The anchor delivery system kit is configurable in such a way that the anchor and suture are disposed within the interior lumen of the elongate cannula. The elongate cannula is disposed within the interior lumen of the delivery conduit. The pushrod is disposed within the interior lumen of the elongate cannula between the anchor and the first end of the elongate cannula. A push force applied to the pushrod causes the pushrod to slide through and push the anchor through and out the tissue piercing tip of the elongate cannula for implantation into tissue.

In accordance with aspects of the present invention, upon removal of the pushrod from the interior lumen of the elongate cannula, a liquid or gel delivered through the supply port can exit the interior lumen of the elongate cannula through the one or more delivery ports and the tissue piercing tip and aperture.

In accordance with an embodiment of the present invention, a method of using an anchor delivery system for incision-less fixation (e.g., sacrospinous) is provided. A vaginal apex region on a vaginal wall is located without making an incision. In accordance with aspects of the present invention, locating the vaginal apex region on the vaginal wall is based on tissue feedback. The vaginal apex region of the vaginal wall is positioned against (adjacent to) a sacrospinous ligament. The anchor delivery system is inserted through the vaginal opening to the vaginal apex region without making an incision. The vaginal apex region and the sacrospinous ligament are pierced through with the elongate cannula in a proximal to distal direction until the cannula reaches the external, distal surface of the sacrospinous ligament. The pushrod is actuated causing the anchor to slide through and out the tissue piercing tip of the elongate cannula to an anchoring location (e.g., on the external, distal surface of the sacrospinous ligament). The anchor delivery system is removed, leaving the anchor disposed in the anchoring location and the suture disposed through the sacrospinous ligament. The loose tail of the suture is anchored to the vaginal apex region of the vaginal wall.

In accordance with aspects of the present invention, the elongate cannula of the anchor delivery system can be withdrawn, after actuating the pushrod, to a position between a proximal surface of the vaginal apex region and the external proximal surface of the sacrospinous ligament. A liquid or gel is supplied, using the anchor delivery system, between the external surface of the vaginal apex region and the external proximal surface of the sacrospinous ligament. In a further aspect, the liquid or gel is an adhesive. The adhesive can be bioglue. In another aspect, the liquid or gel is an agent that increases tissue ingrowth/inflammation.

In accordance with aspects of the present invention, anchoring the loose tail of the suture to the vaginal apex region utilizes locking beads.

In accordance with aspects of the present invention, the anchor is bioabsorbable. In another aspect, the first end of the suture is coupled to the anchor by bonding the first end of the suture to a portion of the anchor (e.g., a groove portion).

In accordance with aspects of the present invention, the second end of the suture is coupled to a ring member of the anchor, e.g. the second end of the suture is threaded through the ring member of the anchor. The second end of the suture can be coupled to one or more anchors having a ring member by threading the second end through the ring member of each of the one or more anchors such that the suture connects each of the one or more anchors.

In accordance with aspects of the present invention, the anchor can be an elongate member having a passageway disposed therethrough along the length of the anchor. In a further aspect, the first end of the suture is threaded through the passageway of the anchor to couple the first end of the suture to the anchor. The threaded first end of the suture is tied to a substantially central portion, between the first end and the second end, of the suture to form a loop. In another aspect, the loop takes on a substantially triangular shape when the anchor is implanted into tissue. The anchor forms the base of the substantially triangular shape.

In accordance with an embodiment of the present invention, multiple anchors can be used to secure the vaginal wall to a sacrospinous ligament. The pushrod is actuated (e.g., actuated to a position sufficient to deploy a first anchor), causing a first anchor coupled with a suture to a second anchor to slide through and out the tissue piercing tip of the elongate cannula to a first anchoring location. The anchor delivery system is withdrawn from the distal surface to the proximal surface of the sacropinous ligament, leaving the first anchor disposed in the first anchoring location. The pushrod is actuated a second time (e.g., completing the actuation or deployment), causing the second anchor coupled with the suture to the first anchor to slide through and out the tissue piercing tip of the elongate cannula to a second anchoring location. The anchor delivery system is removed, leaving the first anchor disposed in the first anchoring location, the second anchor disposed in the second anchoring location, and a midsection, between the first anchor and the second anchor, of the suture disposed through the sacrospinous ligament. The midsection of the suture is anchored to the vaginal apex region of the vaginal wall.

In accordance with an embodiment of the present invention, the anchor delivery system has an anchor having a base section and at least two wing portions affixed to the base section. The wing portions are configured to fold into a substantially straight line along the base section under an appropriate compression force. The anchor is sized, dimensioned, and configured for slidable disposal within and along the interior lumen of the elongate cannula. After the vaginal apex region and sacrospinous ligament is pierced through with the elongate cannula and the elongate cannula is slid from a proximal surface to a desired position on an external, distal surface of the sacrospinous ligament, the pushrod is actuated, causing the anchor to slide through and out the tissue piercing tip of the elongate cannula to an anchoring location. The two wing portions of the anchor unfold outwardly to form a substantially diamond-shape upon release of the compression force. The anchor delivery system is removed, leaving the anchor disposed in the anchoring location. The base section of the anchor is disposed through the sacrospinous ligament and the two wing portions are positioned against the external, distal surface of the sacrospinous ligament. A proximal end, with respect to the anchor delivery system, of the base of the anchor is anchored to the vaginal apex region of the vaginal wall.

In accordance with an embodiment of the present invention, a method of using an anchor delivery system for incision-less sacrospinous fixation includes providing the anchor delivery system having a first arm and a second arm. The anchor delivery system has a first anchor positioned within the first arm and a second anchor positioned within the second arm. A vaginal apex region on the vaginal wall is located without making an incision. The anchor delivery system is inserted through a vaginal opening to the vaginal apex region without making anincision, The vaginal apex region of the vaginal wall is positioned against a sacrospinous ligament using the first arm and the second arm of the delivery system. The first anchor is implanted, using the first arm of the delivery system, into a first section of the vaginal wall proximal to the vaginal apex region and through the sacrospinous ligament. The second anchor is implanted, using the second arm of the delivery system, into a second section of the vaginal wall and proximal to the vaginal apex region and through the sacrospinous ligament. A suture is fastened between the first anchor and the second anchor.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

DETAILED DESCRIPTION

Figure 1:
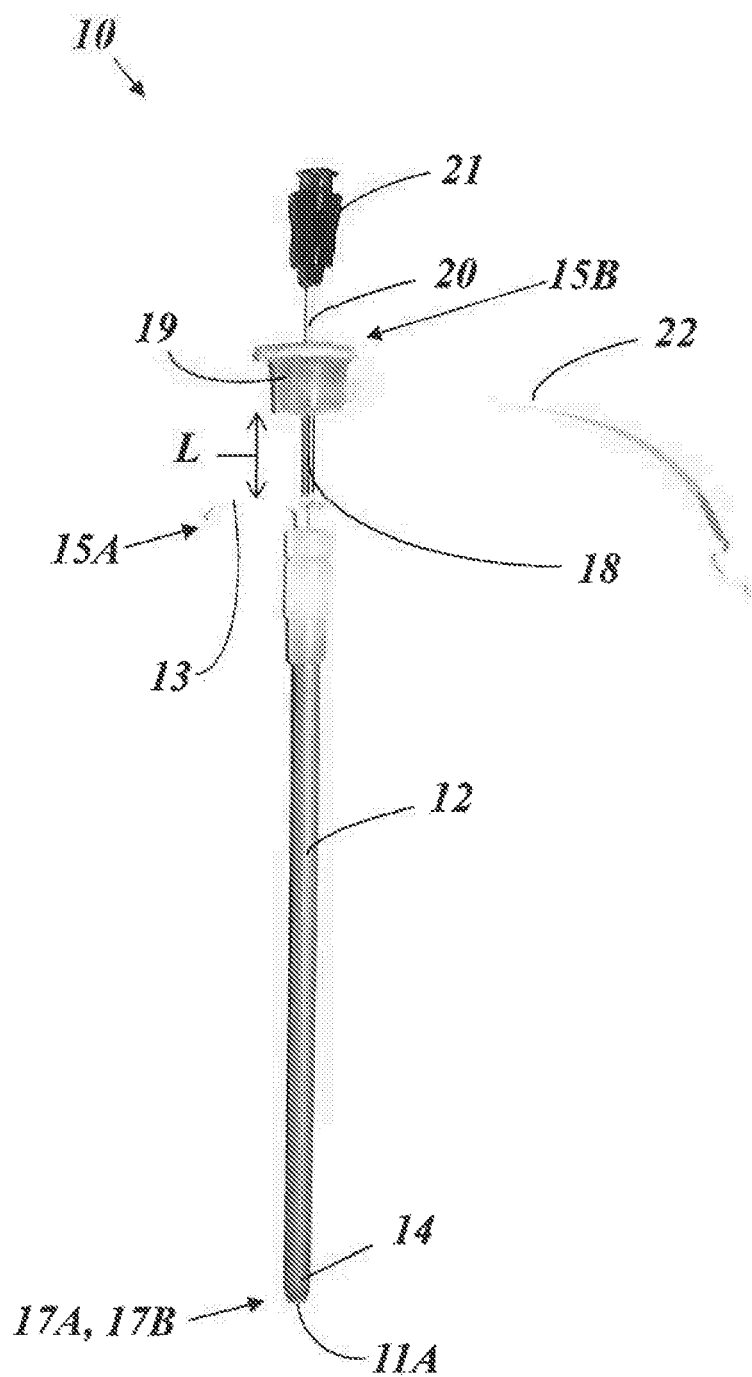
FIG. 1 is a perspective view of an anchor delivery system according to an embodiment of the present invention.

An illustrative embodiment of the present invention relates to an anchor delivery system and method of use. In general, the anchor delivery system integrates an anchor with a specific needle or syringe type device. This anchor delivery system facilitates tissue fixation and enhances scarring and long-term fixation. Although the system is particularly described for use in methods for sacrospinous fixation, it will be understood that the invention is not so limited and can be used in other tissue fixation contexts.

FIGS. 1 through 31, wherein like parts are designated by like reference numerals throughout, illustrate an anchor delivery system and a method of use according to the present invention. Although the present invention will be described with reference to the figures, it should be understood that many alternative forms can embody the present invention. One of ordinary skill in the art will additionally appreciate different ways to alter the parameters disclosed, such as the size, shape, or type of elements or materials, in a manner still in keeping with the spirit and scope of the present invention.

Figure 2:
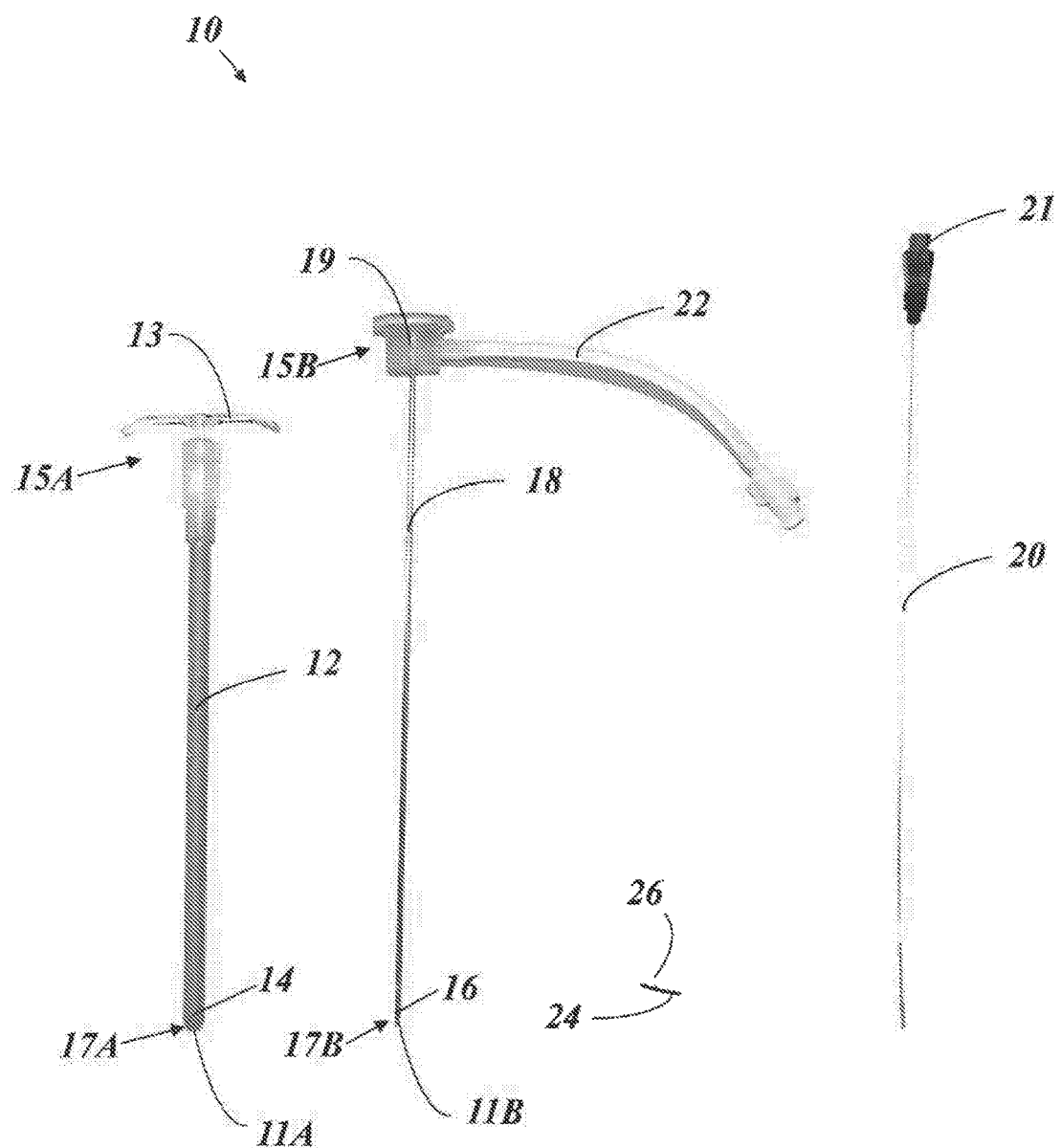
FIG. 2 is a perspective view of the components of the anchor delivery system of FIG. 1 according to one aspect of the present invention.

FIGS. 1-2 illustrate the anchor delivery system 10. FIG. 1 depicts an example anchor delivery system 10 in constructed form. Alternatively, FIG. 2 depicts the separate components of the anchor delivery system or an example of an anchor delivery system kit.

The anchor delivery system 10 has a delivery conduit 12 having a wall forming an interior lumen 11A, a first end 15A, and a second end 17A. The second end 17A terminates with a delivery aperture 14. The delivery conduit 12 can be an outer sheath or a catheter structure. The delivery conduit 12 can include a gripper section 13 for allowing a user to hold the anchor delivery system 10, particularly the delivery conduit 12.

The anchor delivery system 10 has an elongate cannula 18 having a wall sized, dimensioned, and configured for slidable disposal within and along the interior lumen 11A of the delivery conduit 12. The elongate cannula 18 has an interior lumen 11B, a first end 15B, and a second end 17B. The second end 17B terminates with a tissue piercing tip and aperture 16. The elongate cannula 18 can be retracted a certain distance from the delivery conduit 12. In particular, a maximum distance of L between the first end 15A of the delivery conduit 12 and the first end 15B of the elongate cannula 18 may be between about 0.5 centimeters and 1.5 centimeters. The distance of L is meant to provide depth control such that the elongate cannula 18 can only be delivered a certain distance beyond the delivery conduit 12. Other variations of distances may be contemplated by one of skill in the art to provide depth control. In one example, the elongate cannula 18 has a needle-type structure. The elongate cannula 18 can have a pusher section 19 that provides a place for a user to push or place pressure on the elongate cannula 18 during use of the anchor delivery system 10. The pusher section 19 provides a location for a user to grasp and retract the elongate cannula 18 when desired.

The anchor delivery system 10 has a pushrod 20 that is sized, dimensioned, and configured for slidable disposal within and along the interior lumen 11B of the elongate cannula 18. The pushrod 20 can include a handle 21 at a distal end of the pushrod 20 with respect to the delivery aperture 14 and tissue piercing tip and aperture 16. The pushrod 20 can be laterally flexible and axially rigid in use with the anchor delivery system 10.

Figure 3:
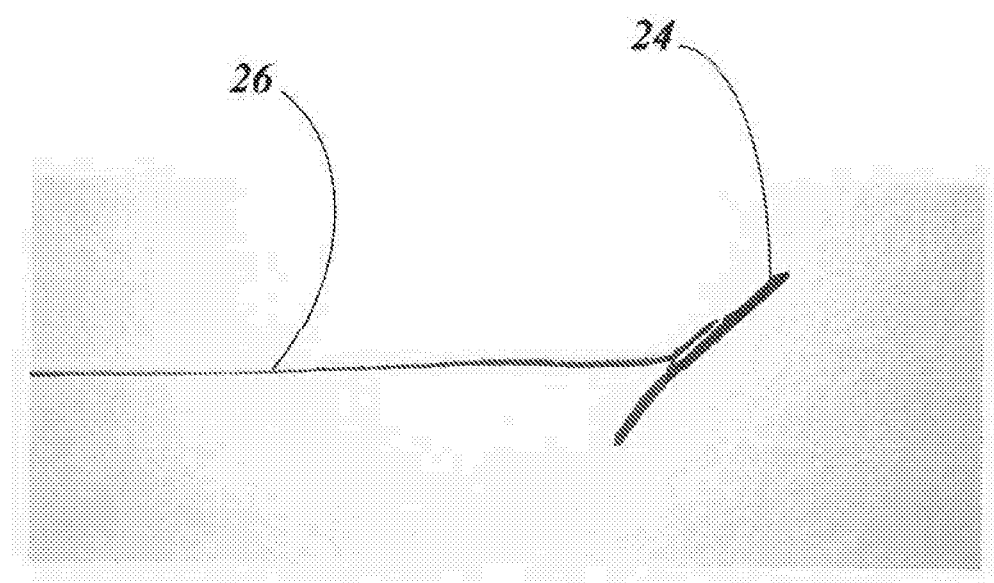
FIG. 3 is a perspective view of an anchor coupled with a suture according to one aspect of the present invention.
Figure 28:
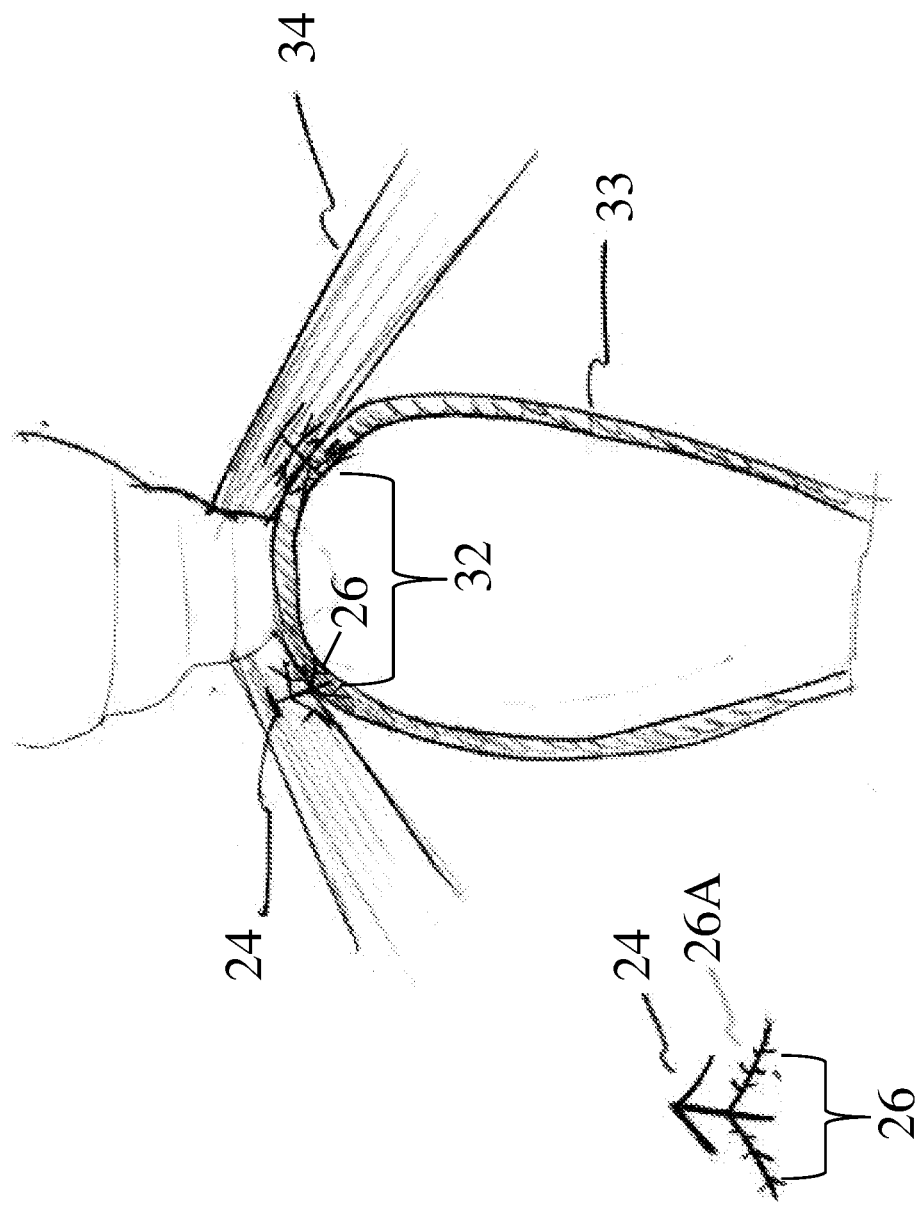
FIG. 28 is a perspective view of an anchor coupled with a barbed suture according to one aspect of the present invention.
Figure 31:
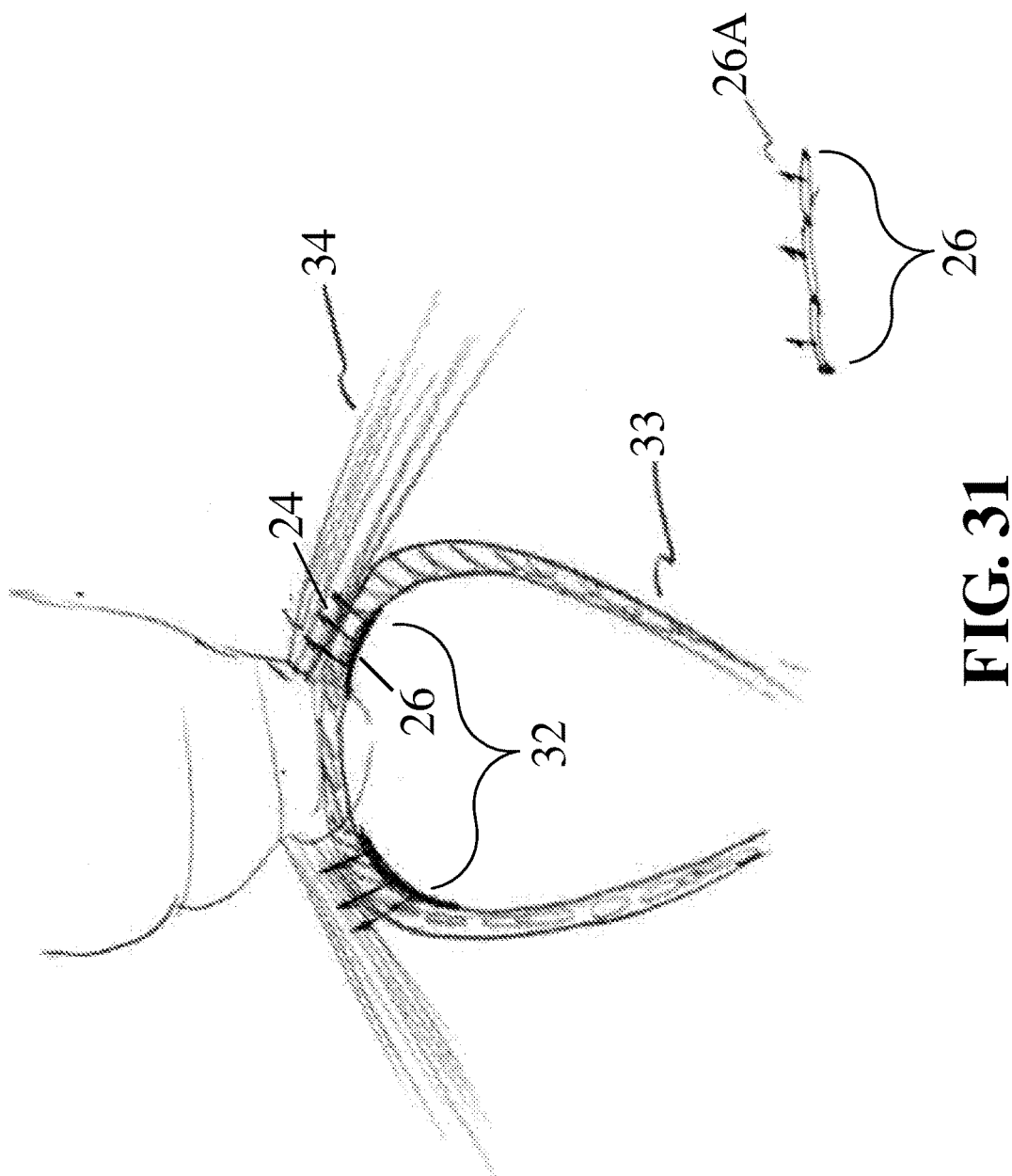
FIG. 31 is a perspective view of an anchor coupled with a suture configured with one or more tines, according to one aspect of the present invention.

The anchor delivery system 10 includes an anchoring unit comprising two portions. The first portion, such as an implant which can be an anchor 24 is coupled with a second portion, a suture 26 as shown in FIGS. 2 and 3. The anchor 24 and suture 26 are sized, dimensioned, and configured to be slidably disposed within and along the interior lumen 11B of the elongate cannula 18. The anchor can be biodegradable, bioabsorbable, or both. Alternatively, the anchor can be made from a material that is permanent and does not degrade in vivo. Additionally, as illustrated in the examples of FIGS. 28 and 31, the suture 26 can include barbs or tines 26A, respectively, along the length of the suture 26.

The anchor delivery system 10 is arranged in such a way that the anchor 24 and suture 26 are disposed within the interior lumen 11B of the elongate cannula 18. The elongate cannula 18 is disposed within the interior lumen 11A of the delivery conduit 12, and the pushrod 20 is disposed within the interior lumen 11B of the elongate cannula 18 between the anchor 24 and the first end 15B of the elongate cannula 18. A push force applied to the pushrod 20, such as the handle 21 of the pushrod 20, causes the pushrod 20 to slide through and deploy the anchor 24 by pushing it through and out of the tissue piercing tip and aperture 16 for implanting at the ligament.

Figure 4:
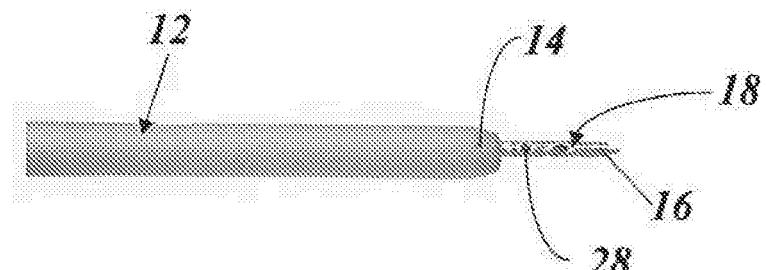
FIG. 4 is a sectional view of an elongate cannula disposed within a delivery conduit of the anchor delivery system according to one aspect of the present invention.
Figure 5A:
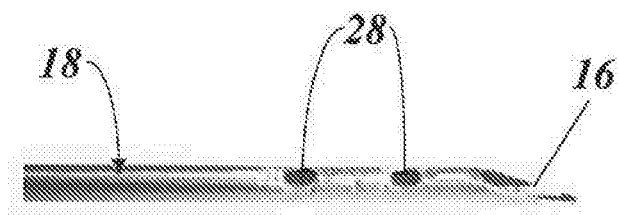
FIG. 5A is a sectional view of the elongate cannula of the anchor delivery system without a pushrod according to one aspect of the present invention.
Figure 5B:
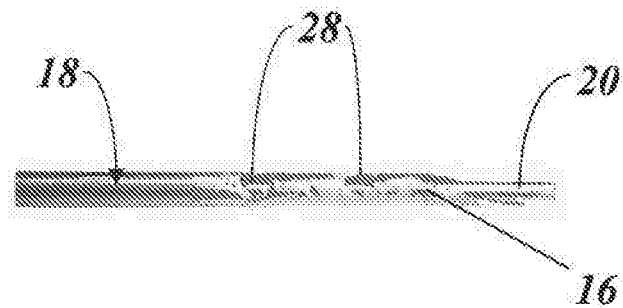
FIG. 5B is a sectional view of the elongate cannula with a pushrod according to one aspect of the present invention.

FIG. 4 depicts a sectional view of the elongate cannula 18 disposed within the delivery conduit 12. In use, the tissue piercing tip and aperture 16 of the elongate cannula 18 can slide along the interior lumen 11A and out through the delivery aperture 14 of the delivery conduit 12. One or more delivery ports 28 can be disposed through the wall of the elongate cannula 18 and proximal to the tissue piercing tip and aperture 16 as shown in FIGS. 5A-5B for delivering a liquid or gel. The delivery ports 28 may be positioned about 2 centimeters from each other along the wall of the elongate cannula 18. FIG. 5B depicts the arrangement of the pushrod 20 within the elongate cannula 18 illustrating how the pushrod 20 functions with the elongate cannula 18 in deploying an anchor from the elongate cannula 18.

Figure 6:
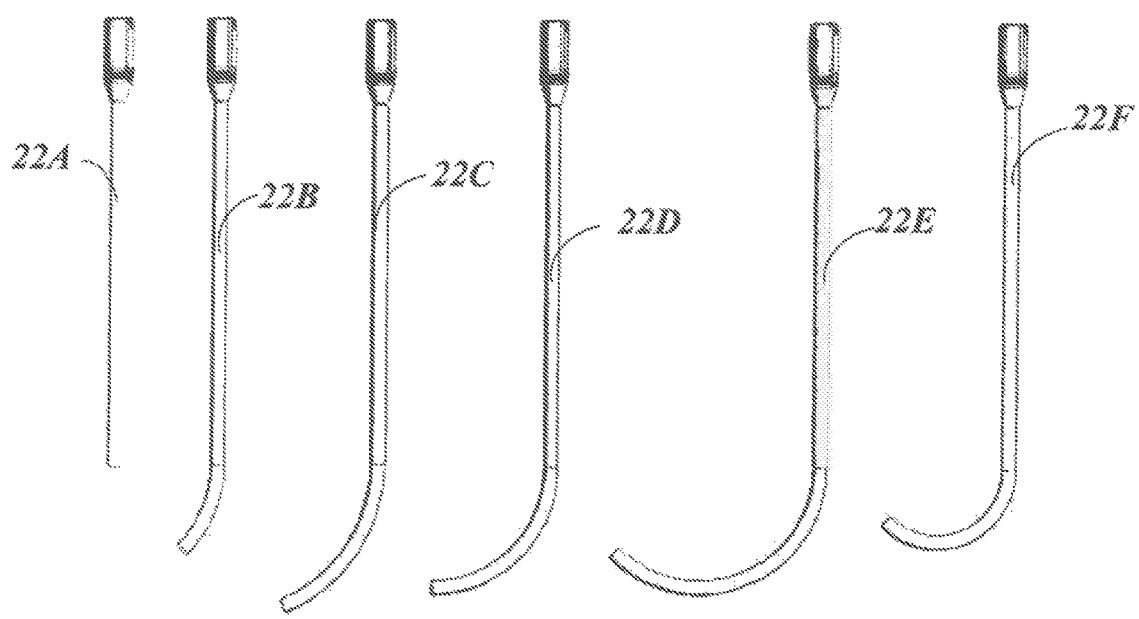
FIG. 6 is a perspective view of supply ports with different curvatures according to one aspect of the present invention.

As shown in FIGS. 1 and 2, the anchor delivery system 10 can have a supply port 22 that is attached into the interior lumen 11B of the elongate cannula 18. In particular, the supply port 22 can be disposed through the wall of the elongate cannula 18 into the interior lumen 11B of the elongate cannula 18 at a location that is distal from the tissue piercing tip and aperture 16. A therapeutic substance, such as a liquid or gel, is supplied to the interior lumen 11B of the elongate cannula 18 through the supply port 22. In another example, the anchor delivery system 10 does not have a supply port 22 and the liquid or gel can be supplied directly to the interior lumen 11B of the elongate cannula 18. Upon removal of the pushrod 20 from the interior lumen 11B of the elongate cannula 18 as shown in FIG. 5A, the liquid or gel can be delivered through the supply port 22 or directly to and through the elongate cannula 18 and can exit the interior lumen 11B of the elongate cannula 18 through the one or more delivery ports 28 (shown in FIGS. 4-5B) and the tissue piercing tip and aperture 16. In one example, the liquid or gel can be an adhesive or glue. In particular, the adhesive may be bioglue (biological glue). Alternatively, the liquid or gel is mesh fluid, sprayed fibrin/thrombin glue, TissuGlu® by Cohera Medical, Inc., etc. In another example, the liquid or gel is an agent that increases tissue ingrowth/inflammation and increases tissue planes. Other properties of the fluid or gel may include biocompatibility, tolerance in a pravaginal/paravesical/pararectal spaces, dual characteristics as scaffold to enable ingrowth and glue for short-term adherence, ease of injection, thick/viscous enough to remain in location of injection, and thin/fluid enough to allow for distribution at injection site enabling broad area of adherence. FIG. 6 depicts supply ports 22A-22F with different curvatures. In particular, the supply ports 22A-22F have curvature angles at one end ranging from about 0 degrees or straight (supply port 22A) to about 90 degrees (supply port 22D) to about 180 degrees (supply port 22F).

Figure 7:
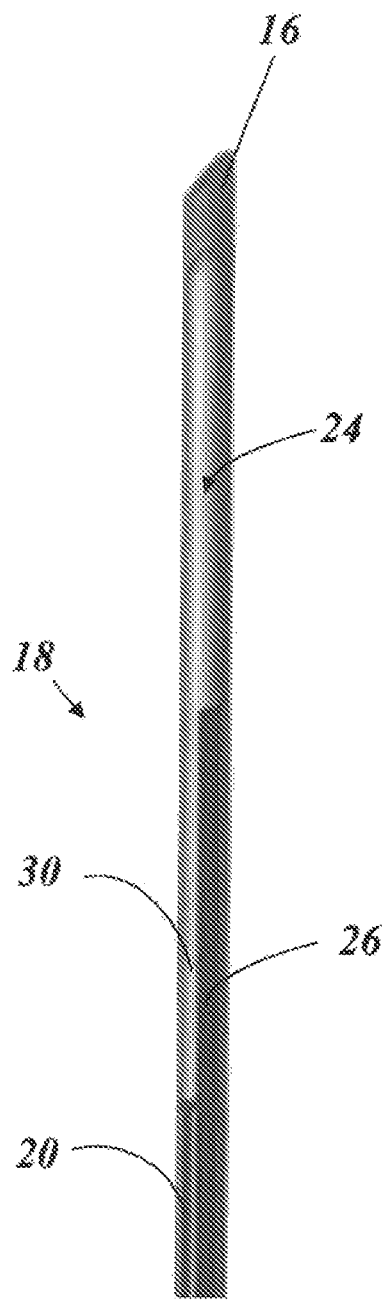
FIG. 7 is a cross-sectional view of the elongate cannula in use according to one aspect of the present invention.

FIG. 7 depicts a cross-sectional view of the elongate cannula 18 in use with an anchor or implant. In this example, the anchor 24 includes a portion such as a groove portion 30 such that a suture 26 is coupled to the anchor 24 by bonding of one end of the suture 26 to the groove portion 30. The anchor may be attached by alternative means than direct bonding. A pushrod 20 is inserted or disposed within the interior lumen 11B of the elongate cannula 18 such that the pushrod 20 engages the groove portion 30 of the anchor. This allows for the pushrod 20 to force the anchor 24 through the elongate cannula 18 and out of the tissue piercing tip and aperture 16.

Figure 8A:
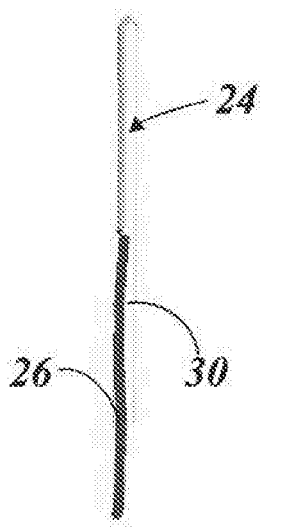
FIG. 8A is a perspective view of an anchor coupled with a suture prior to deployment according to one aspect of the present invention.
Figure 8B:
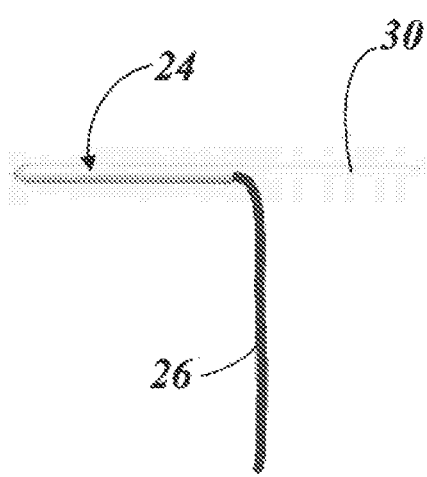
FIG. 8B is a perspective view of the anchor/suture in FIG. 8A after deployment according to one aspect of the present invention.

FIG. 8A depicts an anchoring unit comprising two portions prior to deployment. A first portion, anchor 24, is configured with the groove portion 30 of FIG. 7 and coupled with a second portion, suture 26. For example, the anchor 24 with the attached suture 26 forms this configuration while disposed in the elongate cannula 18 prior to deployment. FIG. 8B depicts the anchor 24 coupled with the suture 26 after deployment in a tissue. In this example, the anchor 24 coupled with the suture 26 forms a T-shape when the anchor 24 is implanted or deployed into the tissue.

Figure 9A:
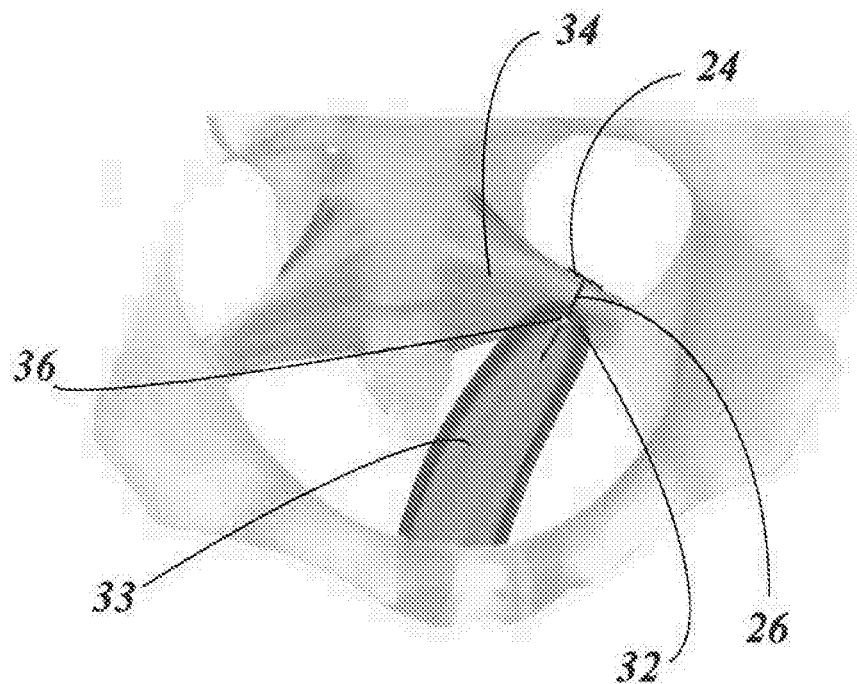
FIGS. 9A-9B are perspective views of the result of a first anchor procedure according to an embodiment of the present invention.
Figure 9B:
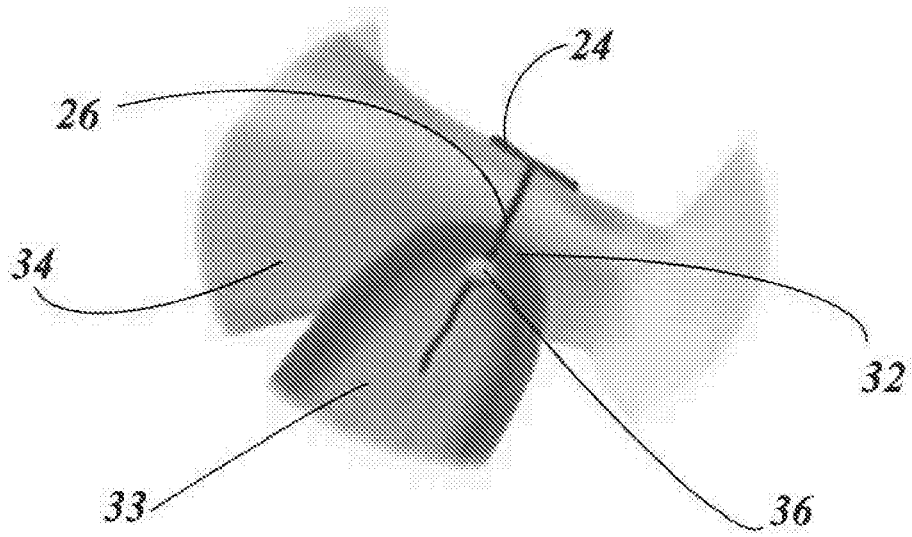

FIGS. 9A-9B depict the result of a first anchor procedure. This first anchor procedure is a method of using the anchor delivery system 10 for incision-less sacrospinous fixation. This first anchor procedure includes providing the anchor delivery system 10 as described above. As shown in FIG. 7, the anchor 24 and suture 26 are sized, dimensioned, and configured for slidable disposal within and along the interior lumen 11B of the elongate cannula 18. As shown in FIGS. 8A-8B, the suture 26 has one end coupled to the anchor 24 and another end forming a loose tail.

In this first anchor procedure, a vaginal apex region 32 on a vaginal wall 33 of the vagina is located without making any incisions. In particular, the vaginal apex region 32 can be located based on tissue feedback. The vaginal apex region 32 is positioned against the sacrospinous ligament 34. The anchor delivery system 10 is inserted through the vaginal opening to the vaginal apex region 32 without making any incisions. The piercing tip and aperture 16 of the elongate cannula 18 pierces through the vaginal apex region 32 and is slid from a proximal surface to a desired position on an external, distal surface of the sacrospinous ligament 34. Alternatively, the piercing tip and aperture 16 at least partially pierce the sacrospinous ligament 34 to deploy the anchor through the pierced vaginal wall and through the at least partially pierced sacrospinous ligament 34.

Figure 29:
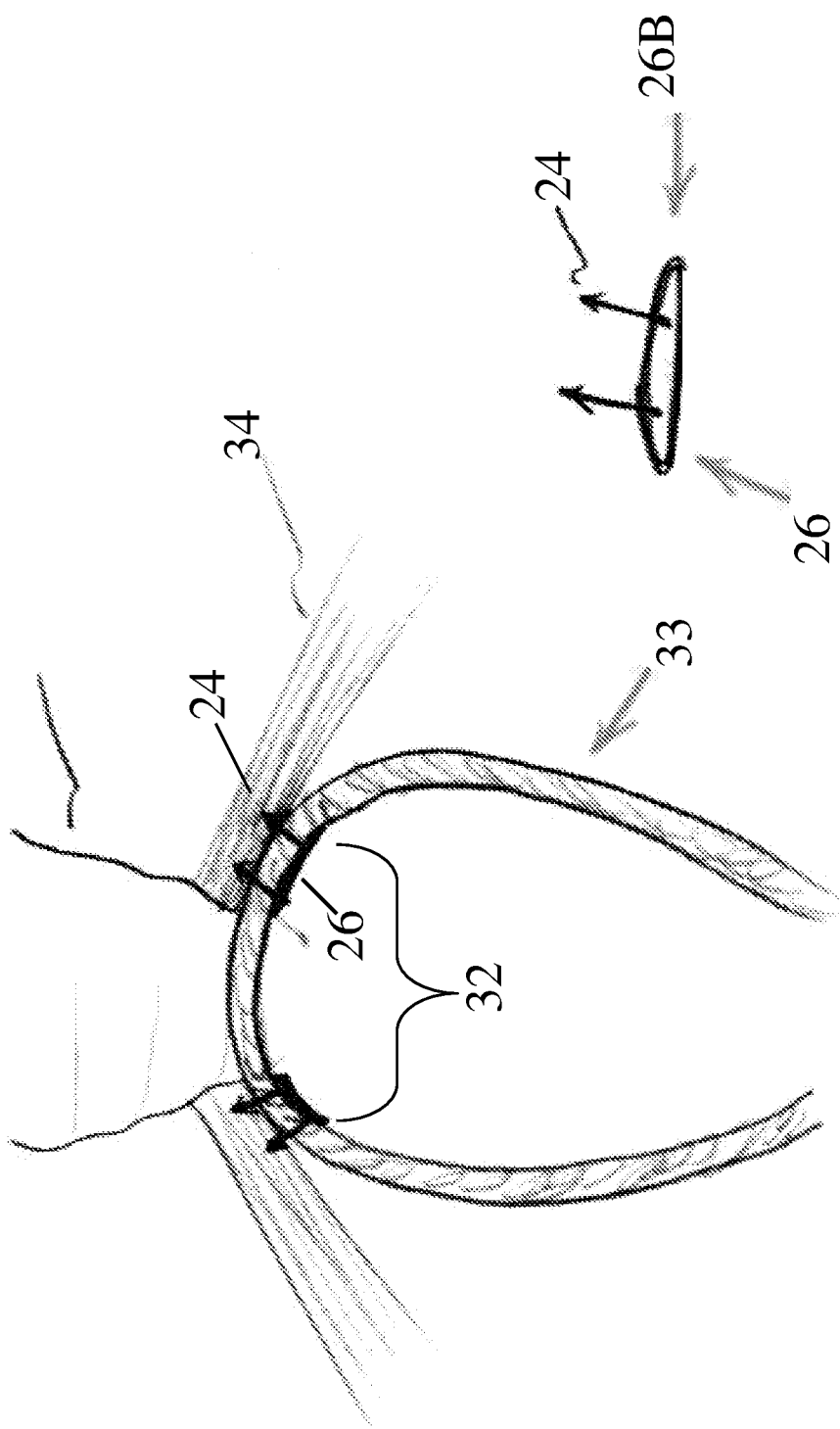
FIG. 29 is a perspective view of an anchor coupled with a washer according to one aspect of the present invention.
Figure 30:
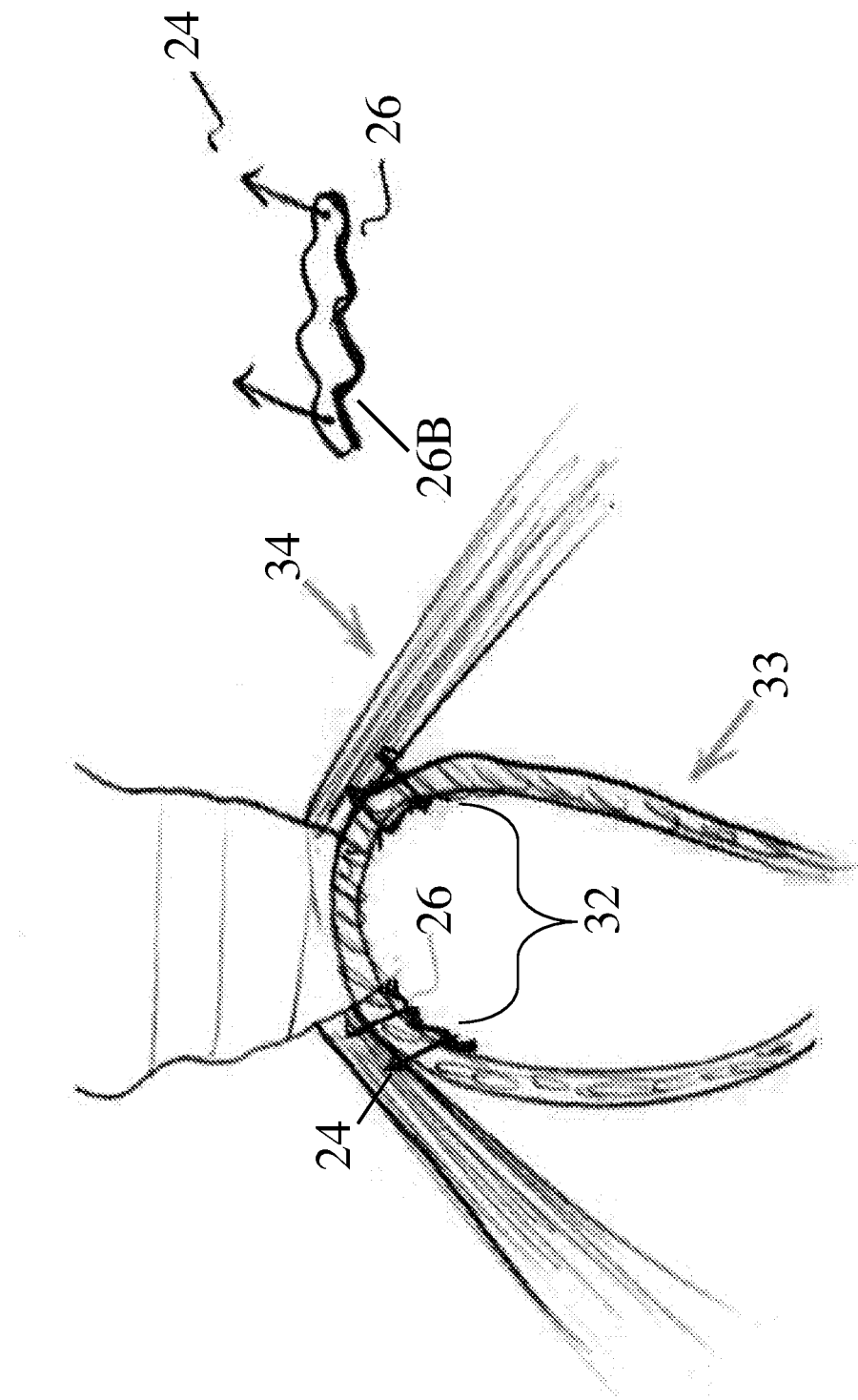
FIG. 30 is a perspective view of an anchor coupled with a corrugated washer according to one aspect of the present invention.

A user can slide the pushrod 20 to cause the anchor 24 to slide through and out of the tissue piercing tip and aperture 16 to an anchoring location near the desired position. When the anchor delivery system 10 is removed, it leaves the anchor 24 disposed in the anchoring location and the suture 26 disposed through the sacrospinous ligament 34 as shown in FIGS. 9A-9B. The loose tail of the suture 26 is anchored to the vaginal apex region 32 of the vaginal wall. For example, the loose tail of the suture 26 can be anchored to the vaginal apex region 32 by using any know fastening mechanism, such as one or more locking beads 36. Additionally, as depicted in FIGS. 29 and 30, suture 26 may be anchored to the vaginal apex region 32 using a washer type mechanism 26B.

This first anchor procedure may further include withdrawing the elongate cannula 18 to a position between the external surface of the vaginal apex region 32 and the external, proximal surface of the sacrospinous ligament 34 (a space between the vaginal apex region 32 and sacrospinous ligament 34). Using the anchor delivery system 10, a liquid or gel is supplied to this space, between the external surface of the vaginal apex region 32 and the external, proximal surface of the sacrospinous ligament 34. The liquid or gel can be an adhesive such as biological glue. In another example, the liquid or gel can be an agent that increases tissue ingrowth/inflammation at this site between the external surface of the vaginal apex region 32 and the external, distal surface of the sacrospinous ligament 34.

Figure 10:
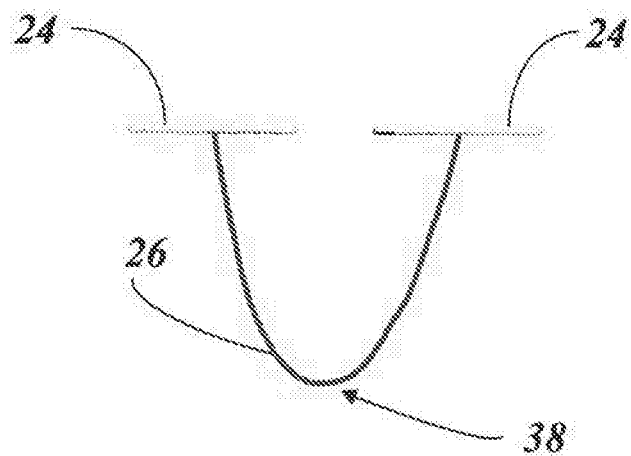
FIG. 10 is a perspective view of two anchors coupled together by a suture after deployment according an embodiment of the present invention.
Figure 11A:
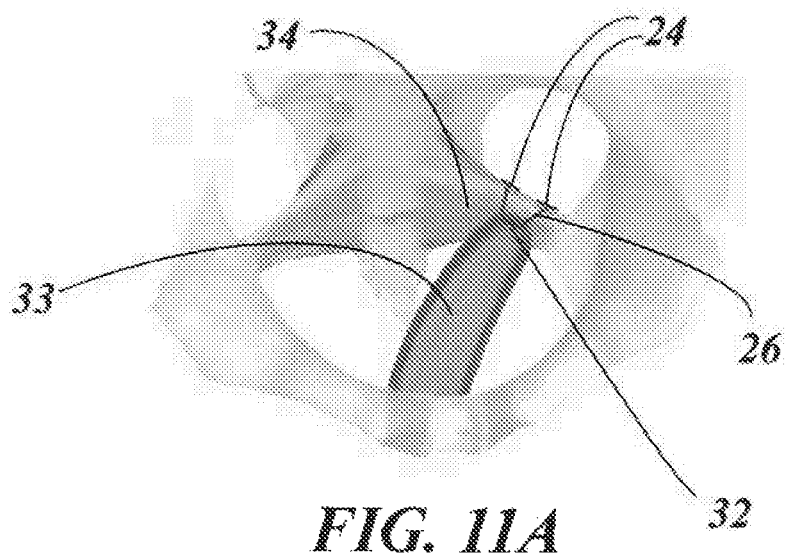
FIGS. 11A-11B are perspective views of the result of a second anchor procedure according to an embodiment of the present invention.
Figure 11B:
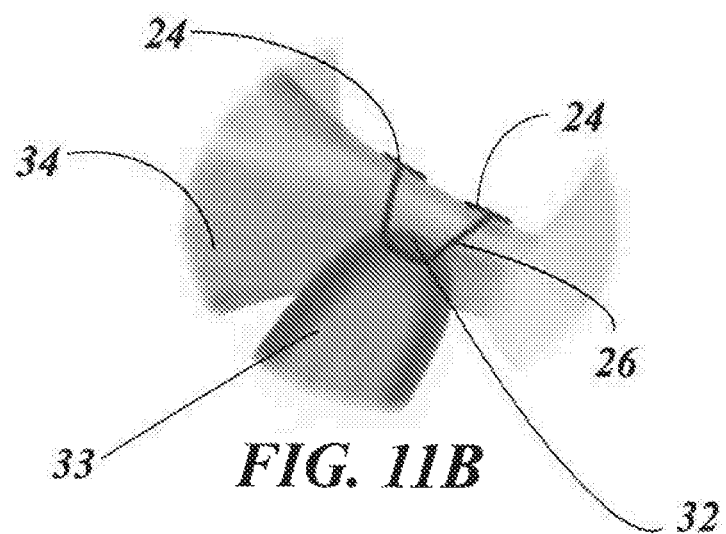

FIG. 10 depicts two anchors 24 coupled together by a suture 26 in a configuration after deployment of the two anchors 24. In this example, two anchors 24 are attached to each other by a suture 26 enabling a partial loop to be formed between the two anchors 24 after deployment of each. This formation is further depicted in FIGS. 11A-11B illustrating results of a second anchor deployment procedure. Similar to the first anchor procedure, an anchor delivery system 10 as described above is initially provided. The two anchors 24 attached with the suture 26 are sized, dimensioned, and configured for slidable disposal within and along the interior lumen 11B of the elongate cannula 18.

Similar to the first anchor procedure, a vaginal apex region 32 on the vaginal wall 33 of the vagina is located without making any incisions. In particular, the vaginal apex region 32 can be located based on tissue feedback. The vaginal apex region 32 is positioned against the sacrospinous ligament 34. The anchor delivery system 10 is inserted through the vaginal opening to the vaginal apex region 32 without making any incisions. The piercing tip and aperture 16 of the elongate cannula 18 pierces through the vaginal apex region 32 and is slid from a proximal surface of the sacrospinous ligament to a desired position on an external, distal surface of the sacrospinous ligament 34.

A user can slide the pushrod 20 to cause one anchor 24 (i.e., first anchor) coupled with the suture 26 to a second anchor 24 to slide through and out of the tissue piercing tip and aperture 16 to a first anchoring location. The anchor delivery system 10 is withdrawn from the distal surface to the proximal surface of the sacrospinous ligament 34, leaving the first anchor 24 disposed in the first anchoring location. The pushrod is actuated or slid, causing the second anchor 24 coupled with the suture 26 to the first anchor 24 to slide through and out the tissue piercing tip and aperture 26 to a second anchoring location. When the anchor delivery system 10 is removed, it leaves one anchor 24 disposed in location, and a midsection 38, between the two anchors 24 as shown in FIG. 10, of the suture 26 disposed through the sacrospinous ligament 34 as shown in FIGS. 11A-11B. In particular, the midsection 38 of the suture 26 is anchored to the vaginal apex region 32 of the vaginal wall.

Figure 12A:
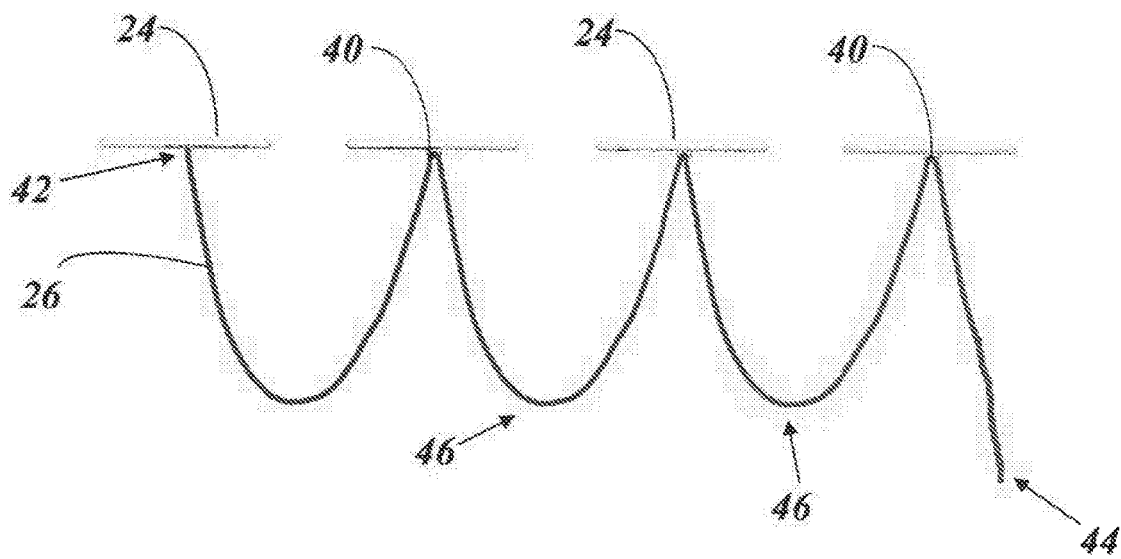
FIG. 12A is a perspective view of multiple anchors coupled together by a suture according to one aspect of the present invention.
Figure 12B:
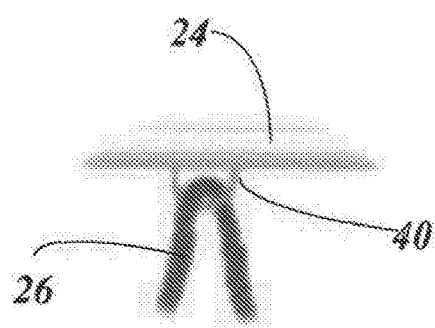
FIG. 12B is a close-up view of the ring-member coupling the suture of FIG. 12A according to one aspect of the present invention.

FIG. 12A depicts multiple anchors 24 coupled together by a suture 26 and ring members 40. In this example, a first end 42 of the suture 26 is coupled to one of the anchors 24. The coupling of the first end 42 can include direct attachment (shown in FIG. 12A) to the anchor 24 or coupling via a ring member 40 of an anchor 24. The second end 44 of the suture 26 or loose end is coupled to a ring member 40 of at least one other anchor 24. In particular, the second end 44 of the suture 26 is threaded through the ring member 40 of the anchor 24 as shown in FIG. 12B. The threaded second end 44 of the suture 26 can then be coupled to additional anchors 24 having ring members 40 by threading the threaded second end 44 through the ring member 40 of each of the additional anchors 24 such that the suture 26 can connect each of the additional anchors 24 (i.e., by forming a partial loop 46) as shown in FIG. 12A. The second end 44 of the suture 26 can be pulled for tightening of the suture 26 across the multiple anchors 24.

Figure 13A:
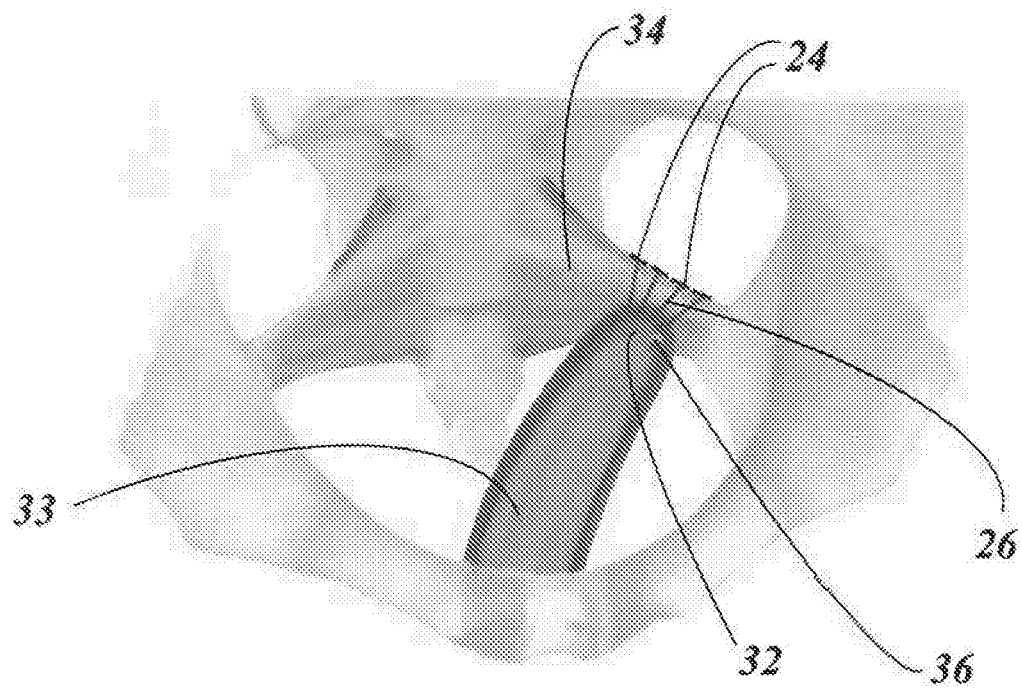
FIGS. 13A-13B are perspective views of the result of a third anchor procedure according to an embodiment of the present invention.
Figure 13B:
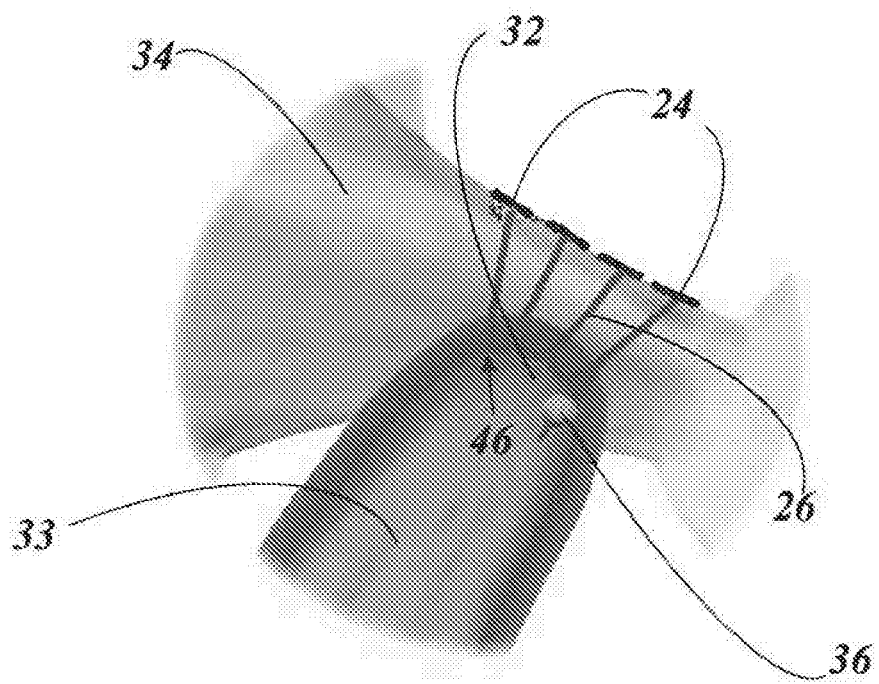

FIGS. 13A-13B depict the result of a third anchor procedure incorporating the multiple anchors 24/ring members 40 configuration shown in FIGS. 12A-12B and described above. The third anchor procedure is similar to the first and second anchor procedures described above. In the third anchor procedure, the multiple anchors 24 with ring members 40 coupled to the suture 26 are sized, dimensioned, and configured for slidable disposal within and along the interior lumen 11B of the elongate cannula 18. In one example, a group of multiple anchors coupled to the suture via ring members may be disposed within the elongate cannula as a group prior to deployment. Alternatively, the multiple anchors with ring members coupled to a suture or not coupled to a suture can be separately disposed within the elongate cannula 18 prior to deployment. The piercing tip and aperture 16 of the elongate cannula 18 is slid from a proximal surface to a desired position on an external, distal surface of the sacrospinous ligament 34.

A user can then slide the pushrod 20 to cause the group of multiple anchors 24 with ring members 40 coupled to the suture 26 to slide through and out of the tissue piercing tip and aperture 16 to Alternatively, the user can slide the pushrod 20 to cause each of the multiple anchors 24 with ring members 40 coupled to the suture 26 or not coupled to the suture 26 to separately or individually slide through and out of the tissue piercing tip and aperture 16. This can be repeated multiple times to position the multiple anchors 24 at multiple anchoring locations on the sacrospinous ligament 34. When the anchor delivery system 10 is removed, the anchor delivery system 10 leaves multiple anchors 24 disposed in multiple anchoring locations with loops 46 between each of the anchors 24 as shown in FIGS. 13A-13B. The loops 46 of the suture 26 can be disposed through the sacrospinous ligament 34. The second end 44 or loose tail of the suture 26 is anchored proximally to the vaginal apex region 32 of the vaginal wall. For example, the second end 44 of the suture 26 can be anchored proximally to the vaginal apex region 32 by using locking beads 36.

Figure 14A:
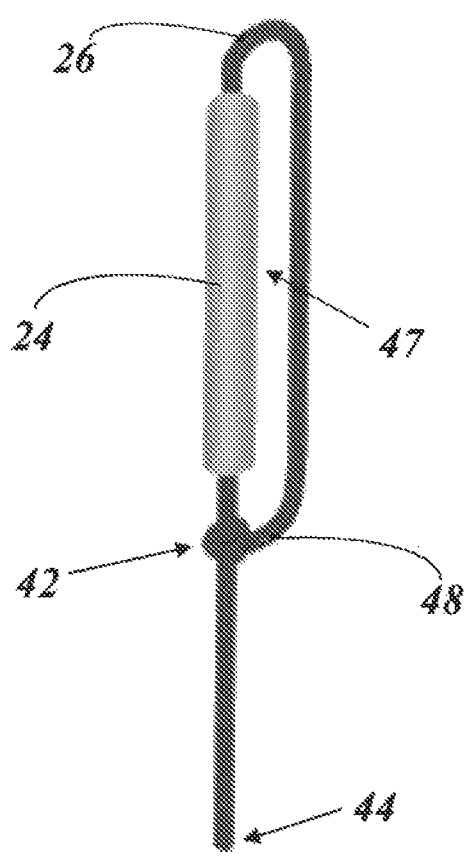
FIG. 14A is a perspective view of another anchor coupled with a suture prior to deployment according to one aspect of the present invention.
Figure 14B:
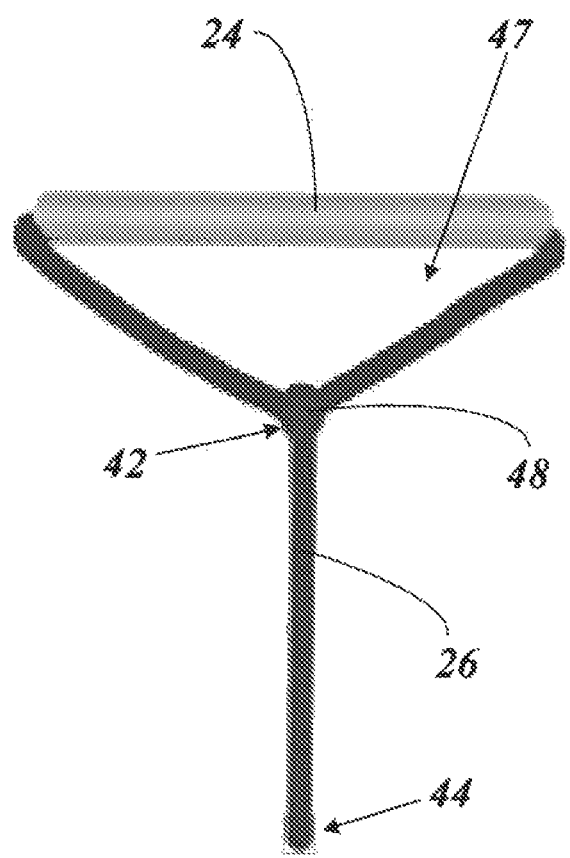
FIG. 14B is a perspective view of the anchor/suture in FIG. 14A after deployment according to one aspect of the present invention.

FIG. 14A depicts another anchor embodiment coupled with a suture 26 prior to deployment. This anchor 24 is an elongate member having a passageway disposed through the anchor 24 along the length of the anchor 24. A first end 42 of the suture 26 is threaded through the passageway of the anchor 24 coupling the first end 42 of the suture 26 to the anchor 24. The threaded first end 42 of the suture 26 is tied to a substantially central portion, between the first end 42 and the second end 44 of the suture 26. In particular, the threaded first end 42 is tied into a knot 48 at the substantially central portion. The anchor 24 coupled with the suture 26 as described above can form a substantially elongate loop 47. In one example, this configuration of the anchor 24 coupled to the suture 26 to form the elongate loop 47 can be disposed in the elongate cannula 18 prior to deployment. FIG. 14B depicts the anchor 24 coupled to the suture 26 in FIG. 14A after deployment in a tissue for example. In this example, the elongate loop 47 takes on or assumes a substantially triangular shape when the anchor 24 is implanted or deployed into tissue. In particular, the anchor 24 forms the base of the substantially triangular shape as shown in FIG. 14 B.

Figure 15A:
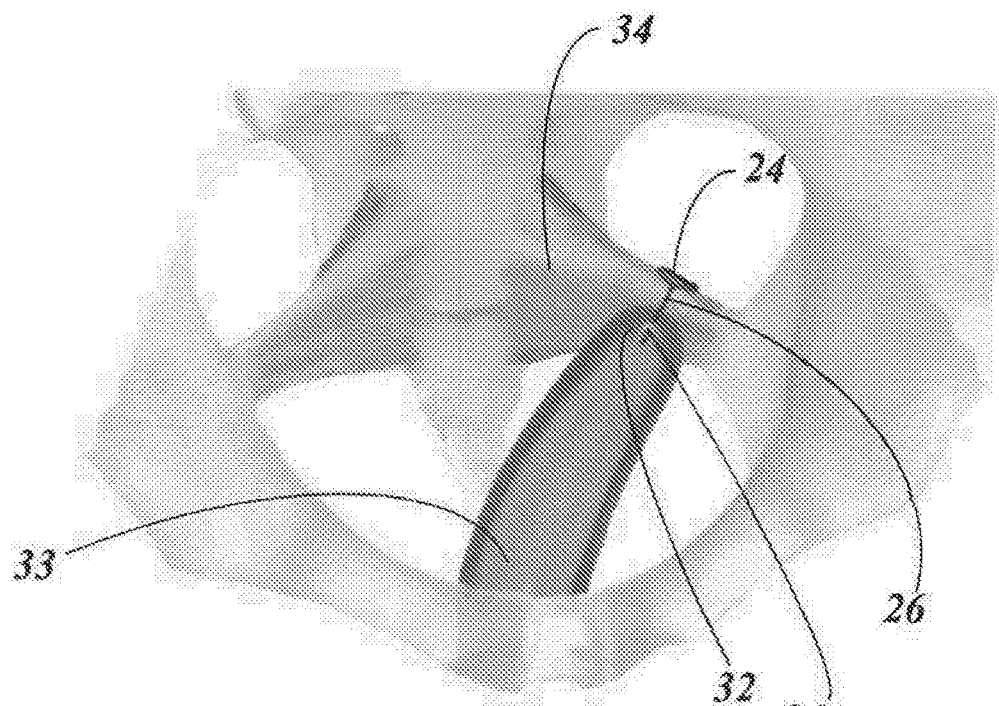
FIGS. 15A-15B are perspective views of the results of a fourth anchor procedure according to an embodiment of the present invention.
Figure 15B:
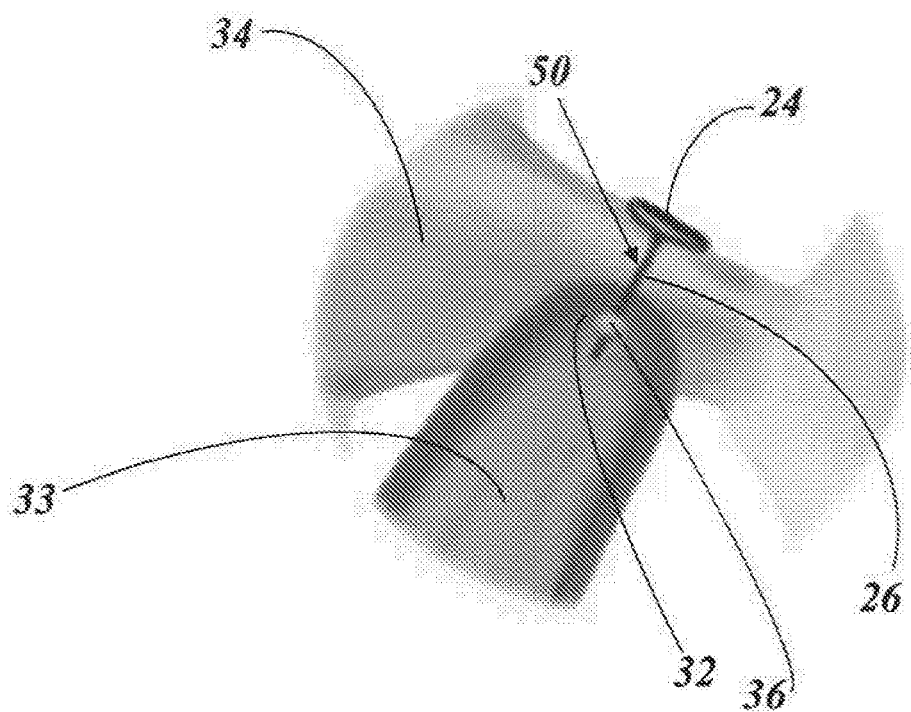

FIGS. 15A-15B depict the result of a fourth anchor procedure incorporating the anchor 24/suture 26 configuration shown in FIGS. 14A-14B and described above. The fourth anchor procedure is similar to the first anchor procedure described above. In the fourth anchor procedure, the anchor 24 coupled to the suture 26 is sized, dimensioned, and configured for slidable disposal within and along the interior lumen 11B of the elongate cannula 18 as shown prior to deployment in FIG. 14A. The piercing tip and aperture 16 of the elongate cannula 18 is slid from a proximal surface to a desired position on an external, distal surface of the sacrospinous ligament 34. A user can slide the pushrod 20 to cause the anchor 24/suture 26 to slide through and out of the tissue piercing tip and aperture 16 to an anchoring location near the desired position. When the anchor delivery system 10 is removed, it leaves the anchor 24 disposed in the anchoring location and the second end portion 50 (i.e., loose tail) of the suture 26 disposed through the sacrospinous ligament 34 as shown in FIG. 9B. This loose tail or second end portion 50 of the suture 26 is anchored to the vaginal apex region 32 of the vaginal wall, such as via any suitable fastening mechanism. In one example, the second end portion 50 of the suture 26 can be anchored to the vaginal apex region 32 by using locking beads 36.

Figures 16A, 16B:
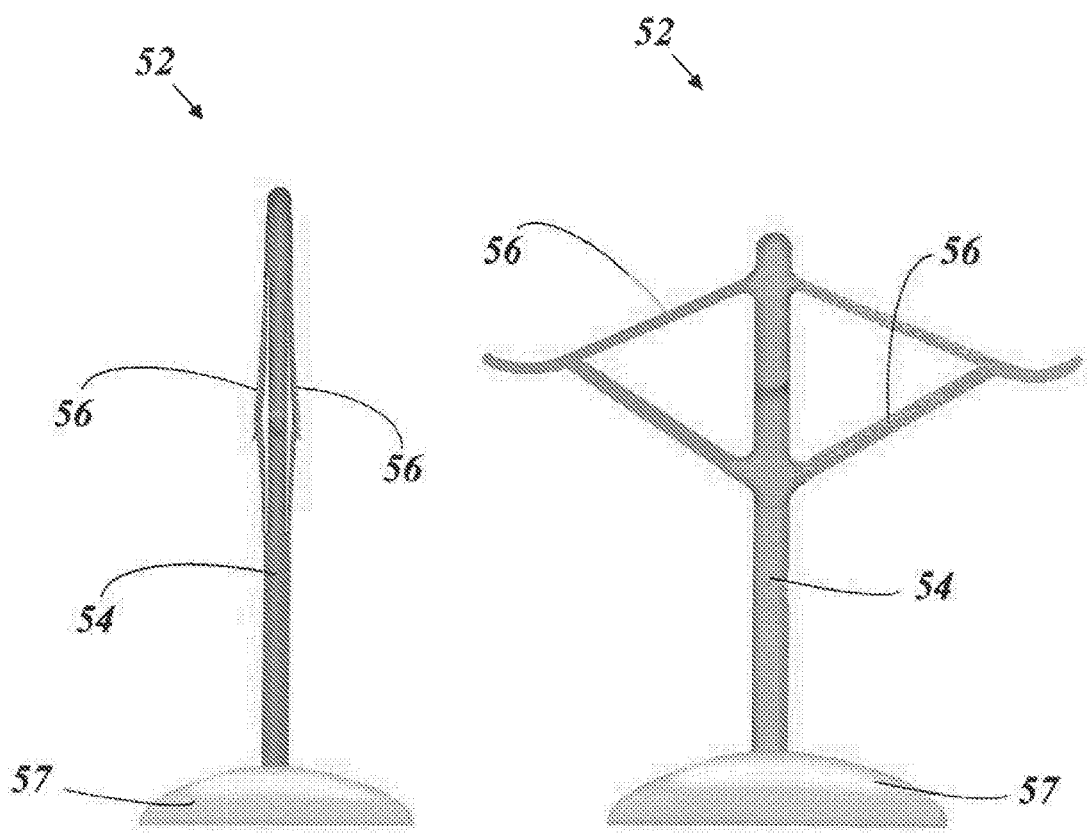
FIG. 16A is a perspective view of a collapsible anchor prior to deployment according to an embodiment of the present invention.
FIG. 16B is a perspective view the collapsible anchor in FIG. 16A after deployment according to one aspect of the present invention.

FIG. 16A depicts a collapsible anchoring mechanism, such as collapsible anchor 52 prior to deployment. FIG. 16B depicts the collapsible anchor in FIG. 16A after deployment. The collapsible anchor 52 is substantially flexible enabling the collapsible anchor 52 to change shape from a formation prior to deployment to a deployed formation. The collapsible anchor 52 has a base section 54 and at least two wing portions 56 affixed to the base section 54. The wing portions 56 are configured to fold into a substantially straight line along the base section 54 as shown in FIG. 16A under suitable compression force, prior to deployment. This allows for the collapsible anchor 52 to be disposed in the elongate cannula 18 prior to deployment. FIG. 16B depicts the collapsible anchor 52 in a formation after deployment. In this example, the two wing portions 56 of the collapsible anchor 52 unfold outwardly from the base section 54 to form a substantially diamond-shape. The collapsible anchor 52 includes a stopper section 57 at the bottom of the base section 54 for anchoring to a tissue.

Figure 17A:
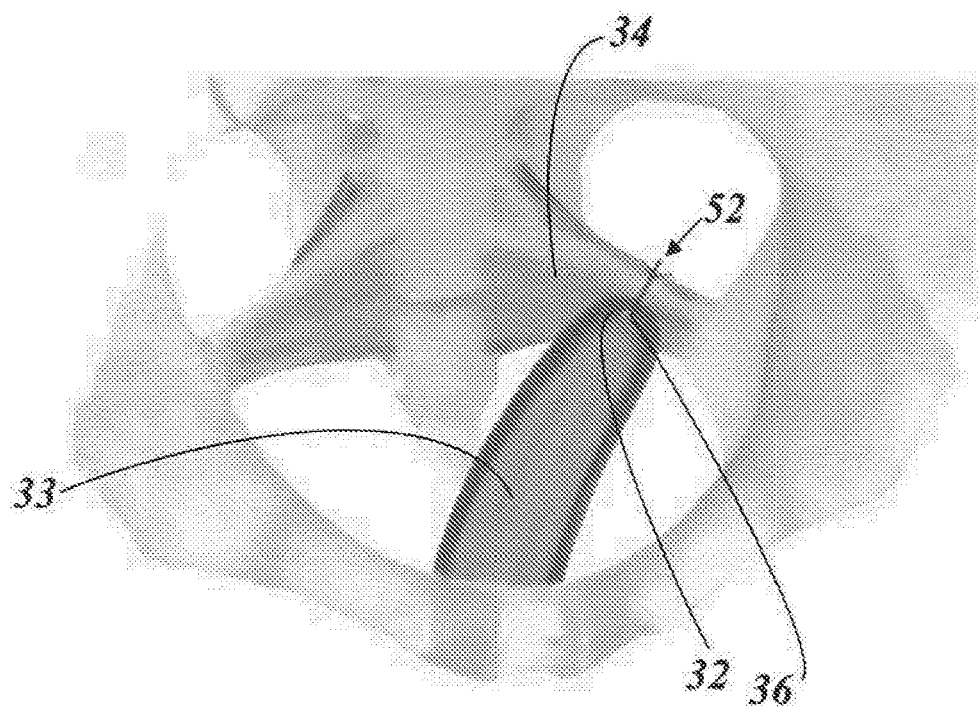
FIGS. 17A-17B are perspective views of the result of a fifth anchor procedure according to an embodiment of the present invention.
Figure 17B:
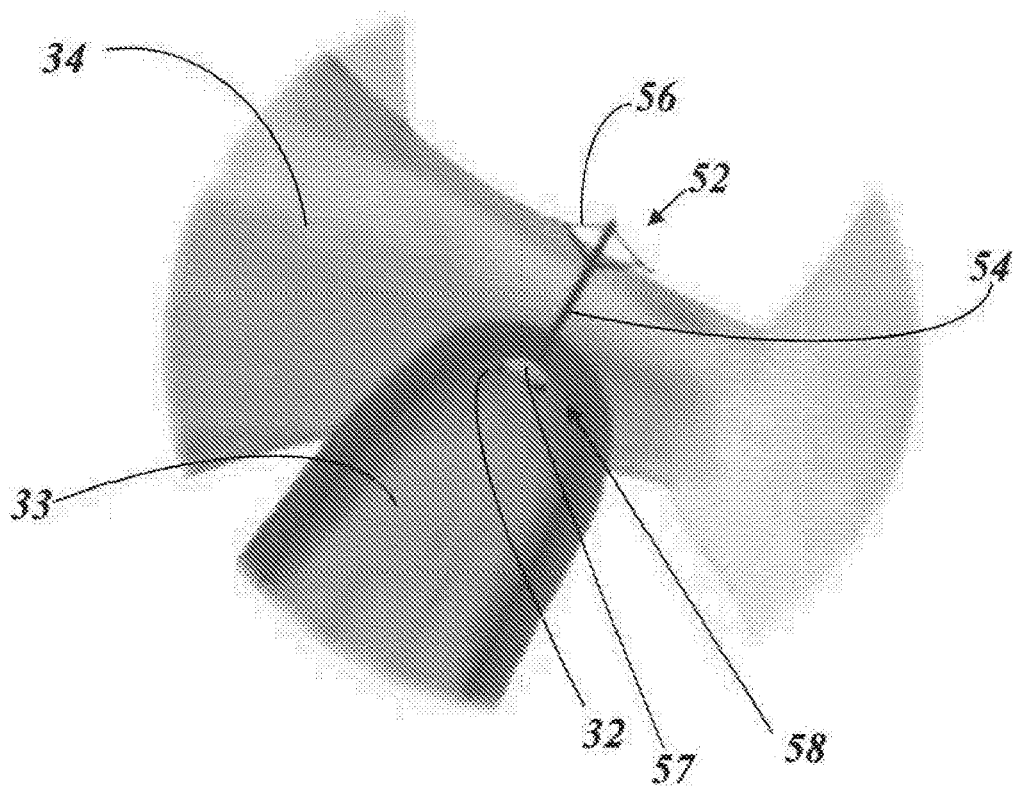

FIGS. 17A-17B depict the result of a fifth anchor procedure incorporating the collapsible anchor 52 shown in FIGS. 16A-16B and described above. The fifth anchor procedure is similar to the first anchor procedure described above. However, this example procedure or result does not include a suture. In the fifth anchor procedure, the collapsible anchor 52 is sized, dimensioned, and configured for slidable disposal within and along the interior lumen 11B of the elongate cannula 18 as shown prior to deployment in FIG. 16A. The vaginal apex region and sacrospinous ligament is pierced through by the piercing tip and aperture 16 of the elongate cannula 18 and the elongate cannula 18 is slid to a desired position on an external, distal surface of the sacrospinous ligament 34. A user can slide the pushrod 20 to cause the collapsible anchor 52 to slide through and out of the tissue piercing tip and aperture 16 to an anchoring location near the desired position. The two wing portions 56 of the collapsible anchor 52 unfold outwardly to form a substantially diamond-shape upon exiting the tissue piercing tip and aperture 16 of the elongate cannula 18. When the anchor delivery system 10 is removed, it leaves the collapsible anchor 52 disposed in the anchoring location. In particular, the base section 54 of the collapsible anchor 52 is disposed through the sacrospinous ligament 34 and the two wing portions 56 are positioned against the external, distal surface of the sacrospinous ligament 34 as shown in FIGS. 17A-17B. A distal end 58, with respect to the sacrospinous ligament 34, of the base section 54 of the collapsible anchor 52 is anchored to the vaginal apex region 32 of the vaginal wall. In particular, the stopper section 57 can be used at the distal end 58 for anchoring the base section 54 to the vaginal apex region 32.

Figure 18A:
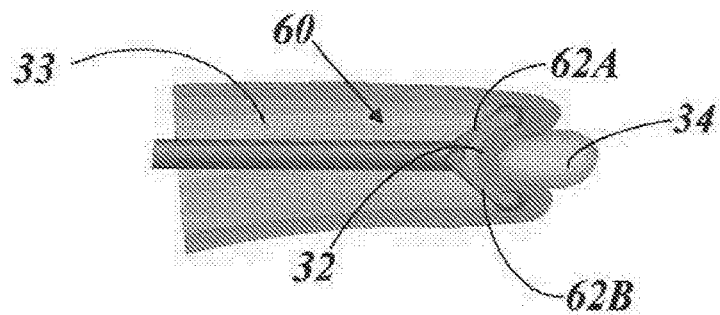
FIGS. 18A-18C are perspective views of a sixth anchor procedure according to an embodiment of the present invention.
Figure 18B:
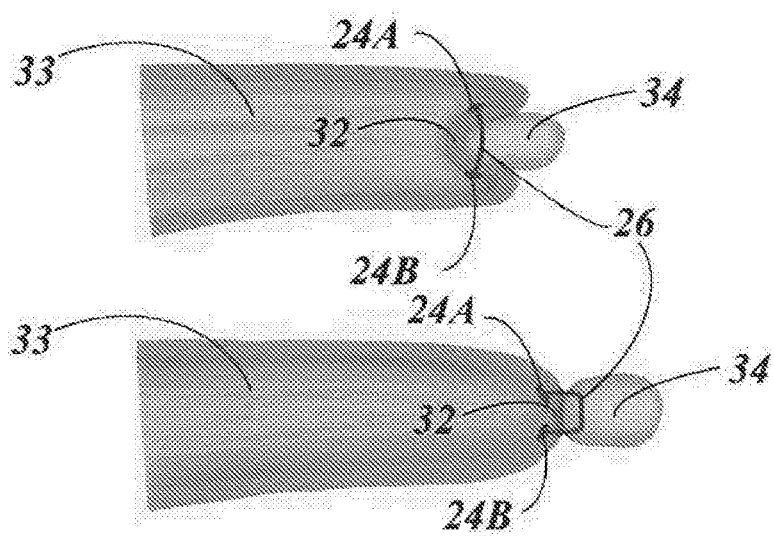
Figure 18C:
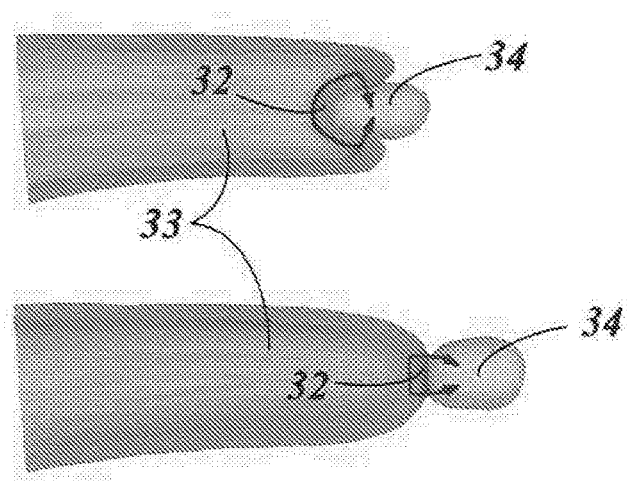

FIGS. 18A-18C depict a sixth anchor procedure. Similar to the procedures described above, the sixth anchor procedure is a method of using an anchor delivery system for incision-less sacrospinous fixation. Initially, a grasper anchor delivery device 60 or grabber device is provided. The grasper anchor delivery device 60 has a first arm 62A and a second arm 62B. A first anchor 24A is positioned within the first arm 62A and a second anchor 24B is positioned within the second arm 62B. As similarly described above, the vaginal apex region 32 on the vaginal wall 33 is located without making any incisions. The grasper anchor delivery device 60 is inserted through the vaginal opening to the vaginal apex region 32 without making any incisions. The vaginal apex region 32 of the vaginal wall 33 is positioned against the sacrospinous ligament 34 using the first arm 62A and the second arm 62B. In particular, the first arm 62A and second arm 62B grasp a portion of the vaginal wall 33 proximal the vaginal apex region 32 and surround the sacrospinous ligament 34 as shown in FIG. 18A. The first anchor 24A is implanted, using a first piercing tip configured with the first arm 62A of the grasper anchor delivery device 60, to a first section of the vaginal wall, proximal to the vaginal apex region 32, through the sacrospinous ligament 34, as described above with respect to FIGS. 1-17B.

Similarly, the second anchor 24B is implanted, using a second piercing tip configured with the second arm 62B of the grasper anchor delivery device 60, to a second section of the vaginal wall 33, proximal to the vaginal apex region 32, through the sacrospinous ligament 34. A suture 26 is fastened between the first anchor 24A and the second anchor 24B through the sacrospinous ligament 34 as shown in FIGS. 18A-18B. Alternatively, the suture 26 can be fastened prior to deployment of the first anchor 24A and the second anchor 24B. The upper figure of FIG. 18B depicts the position of the vaginal apex region 32 with respect to the sacrospinous ligament 34 when the first anchor 24A and second anchor 24B are being implanted or deployed by the grasper anchor delivery device 60. The lower figure of FIG. 18B depicts the position of the vaginal apex region 32 with respect to the sacrospinous ligament 34 after the first anchor 24A and second anchor 24B are implanted. FIG. 18C depicts the position of the vaginal apex region 32 with respect to the sacrospinous ligament 34 based on the forces, as shown by the arrows, provided by the grasper anchor delivery device 60 and anchors 24A, 24B/suture 26 during implanting (upper figure) and after implanting (lower figure).

Figure 19:
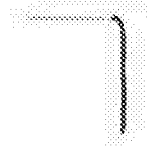
FIG. 19 is a table depicting the results of the six anchor procedures.
Figure 19:
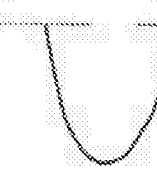
Figure 19:
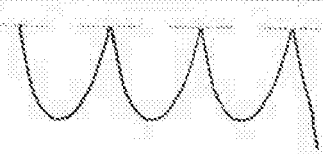
Figure 19:
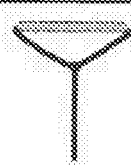
Figure 19:
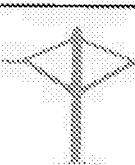
Figure 19:
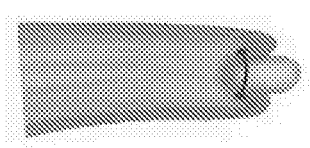

FIG. 19 is a table depicting the results of the six anchor procedures discussed above. In particular, the table illustrates embodiments 1-6 which correlate with the results of anchor procedures one through six respectively.

Figure 20A:
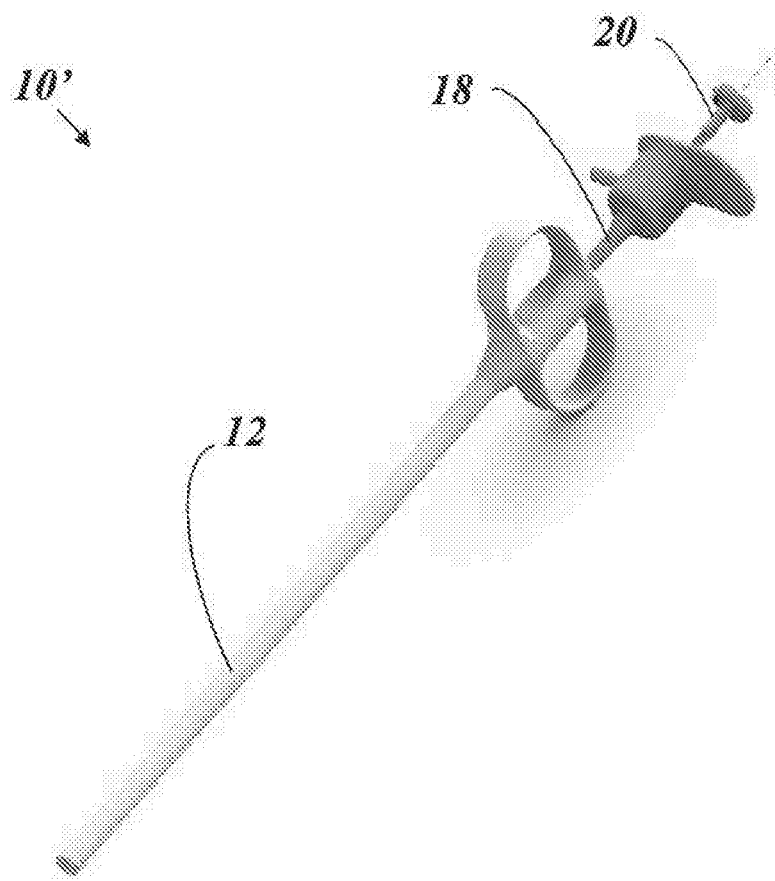
FIG. 20A is perspective views of another anchor delivery system according to an embodiment of the present invention.
Figure 20B:
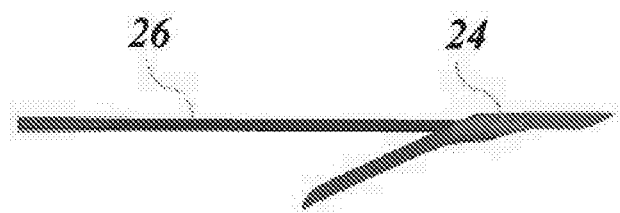
FIG. 20B is a perspective view of another anchor coupled with a suture after deployment according to one aspect of the present invention.

FIG. 20A depicts another anchor delivery system 10' having essentially the same components compared to the anchor delivery system 10 in FIG. 1. The anchor delivery system 10' has a slightly varied design. In general, the anchor delivery system 10' has a delivery conduit 12, elngate cannula 18, and pushrod 20 having similar functions and interactions as described above. FIG. 20B depicts another anchor 24 coupled with a suture 26, similar to the anchor 24/suture 26 of FIG. 3, after deployment by the anchor delivery system 10'.

Figure 21:
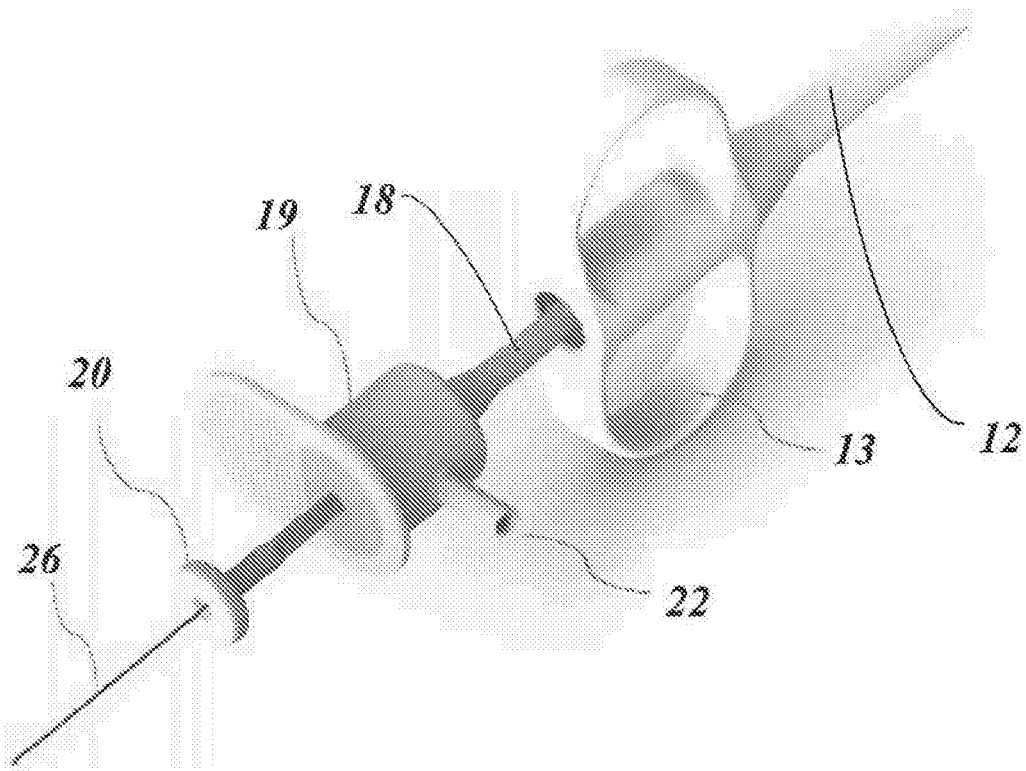
FIG. 21 is a close-up view of a proximal end of the anchor delivery system of FIG. 20A according to one aspect of the present invention.

FIG. 21 depicts a proximal end of the anchor delivery system 10' of FIG. 20A. Similar to the anchor delivery system 10 in FIG. 1, the anchor delivery system 10' includes a delivery conduit 12 with a gripper section 13. In particular, the gripper section 13 is a finger grip surrounding the delivery conduit 12. The anchor delivery system 10' has an elongate cannula 18 with a pusher section 19. In this example, the supply port 22 is configured or molded into the pusher section 19 of the elongate cannula 18 for delivering or injecting a liquid or gel such as an adhesive. The anchor delivery system 10' includes pushrod 20 that is used for deploying an anchor or implant. A suture 26 can be positioned through an interior lumen of the pushrod 20. This suture 26 attaches to an anchor 24 inside the elongate cannula 18.

Figure 22:
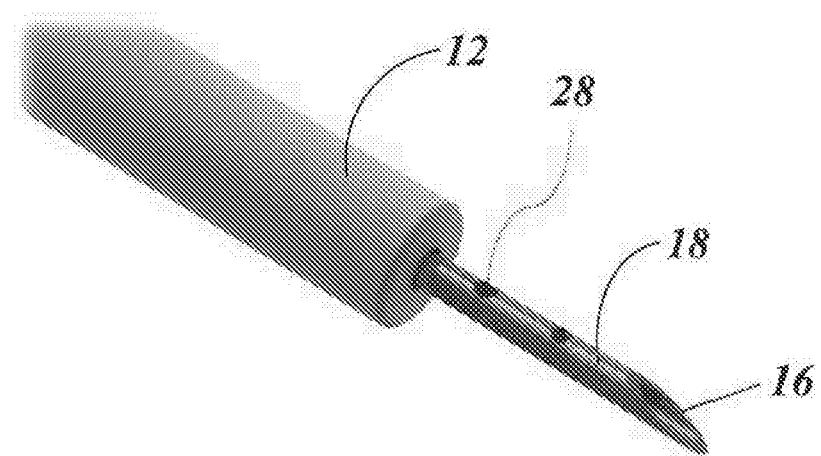
FIG. 22 is a close-up view of a distal end of the anchor delivery system of FIG. 20A according to one aspect of the present invention.

FIG. 22 depicts a distal end of the anchor delivery system 10' of FIG. 20A. Similar to FIG. 4, the anchor delivery system 10' has an elongate cannula 18 disposed within the delivery conduit 12. One or more delivery ports 28 are disposed through the wall of the elongate cannula 18 and proximal to the tissue piercing tip and aperture 16 for delivering a liquid or gel such as adhesive.

Figure 23:
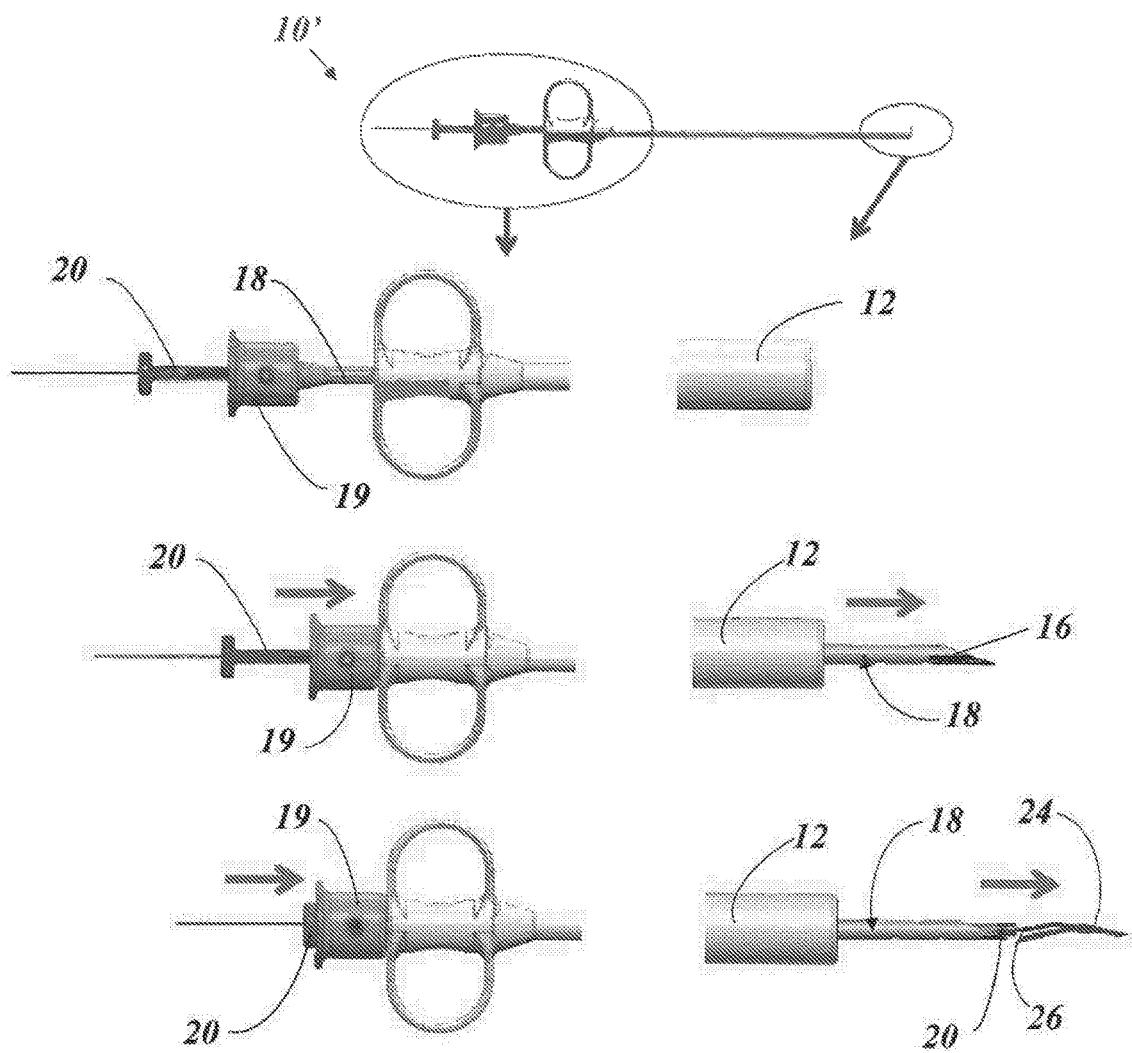
FIG. 23 is perspective views of the anchor delivery system of FIG. 20A in use according to aspects of the present invention.

FIG. 23 depicts the anchor delivery system 10' of FIG. 20A in use. In particular, FIG. 23 illustrates how use of the proximal end in FIG. 21 impacts the function of the components of the distal end in FIG. 22. Initially, the elongate cannula 18 is completely retracted and the pushrod 20 is completely retracted. Then, the pusher section 19 is pushed forward causing the elongate cannula 18 to slide forward and beyond the delivery conduit 12 to a desired position on a tissue such as the sacrospinous ligament. The pushrod 20 is pushed forward to engage an anchor 24/suture 26 causing the anchor 24/suture 26 to slide through and out of the tissue piercing tip and aperture 16 of the elongate cannula 18 to an anchoring location. As shown in FIG. 23, this procedure allows for the anchor delivery system 10' to deploy or implant the anchor 24.

Figure 24A:
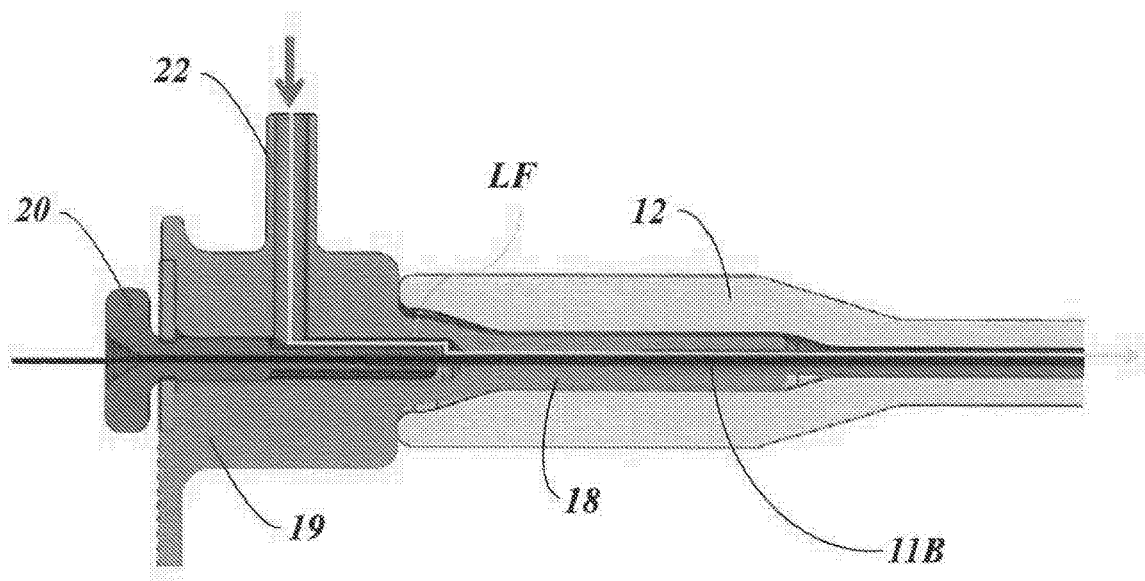
FIG. 24A is a close-up cross-sectional view of a proximal end of the anchor delivery system of FIG. 20A according to one aspect of the present invention.
Figure 24B:
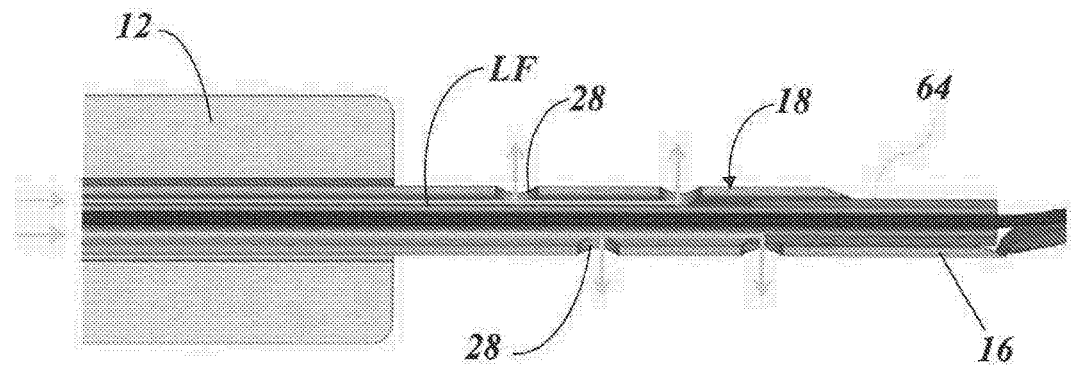
FIG. 24B is a close-up cross-sectional view of a distal end of the anchor delivery system of FIG. 20A in use according to an embodiment of the present invention.

FIG. 24A depicts a proximal end of the anchor delivery system 10' of FIG. 20A. FIG. 24B depicts a distal end of the anchor delivery system 10' of FIG. 20A in use. In particular, FIGS. 24A-24B illustrate the process of delivery the liquid or gel. As shown in FIG. 24A, a liquid or gel is supplied to the interior lumen 11B of the elongate cannula 18 through the supply port 22. In particular, the liquid or gel, such as glue, is injected using a syringe and tube to the supply port 22. A liquid flow LF is shown from the supply port 22 through the pusher section 19 and through the elongate cannula 18 and the delivery conduit 12. The liquid flow LF continues through the distal end of the anchor delivery system 10'. In particular, liquid or gel can exit the interior lumen 11B of the elongate cannula 18 through one or more delivery ports 28 that are disposed through the wall of the elongate cannula 18 and proximal to the tissue piercing tip and aperture 16 as described above. A stopper 64 can be provided at the distal end of the elongate cannula 18 to prevent accidental delivery of glue from the tissue piercing tip and aperture 16.

Figure 25B:
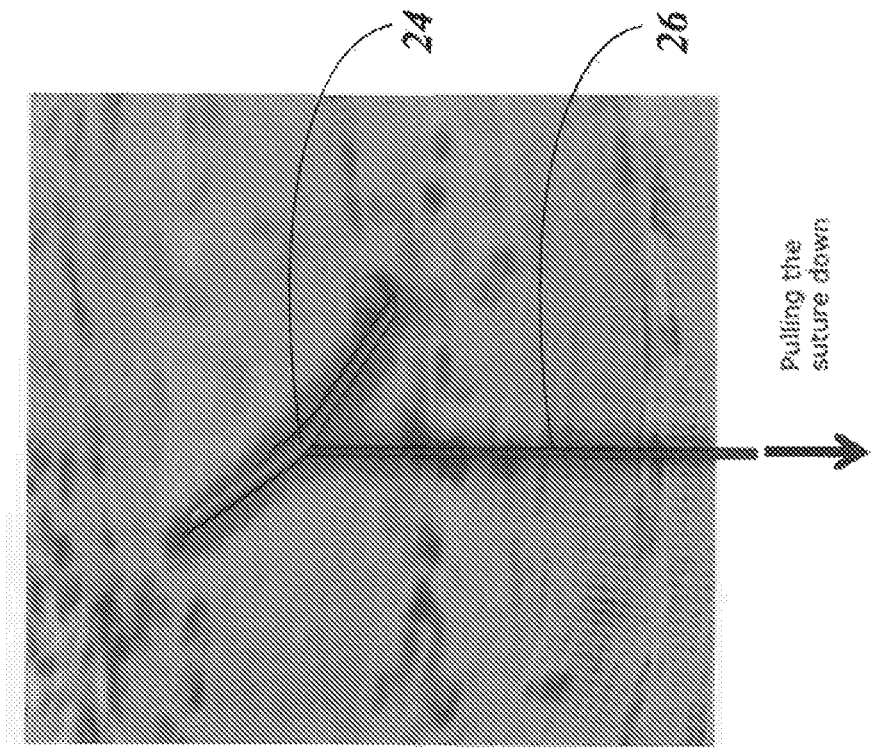
FIG. 25B is a microscopic view of the anchor/suture of FIG. 25A when the suture is pulled in a particular direction according to one aspect of the present invention.
Figure 25A:
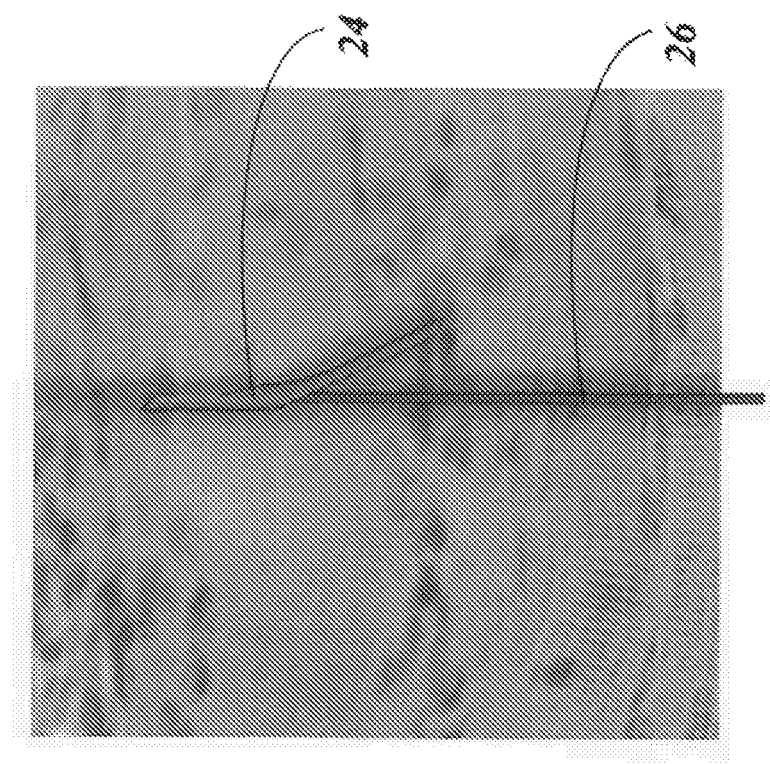
FIG. 25A is a microscopic view of an anchor/suture shortly after deployment according to one aspect of the present invention.

FIG. 25A depicts a microscopic view of the anchor 24/suture 26 shortly after deployment at a tissue such as the sacrospinous ligament. As the suture 26 is pulled in a direction away from the anchor 24, as shown in FIG. 25B, it causes the anchor 24/suture 26 to form the T-shape which allows for the anchor 24 to maintain its position in holding a particular organ/tissue in place.

Figure 26:
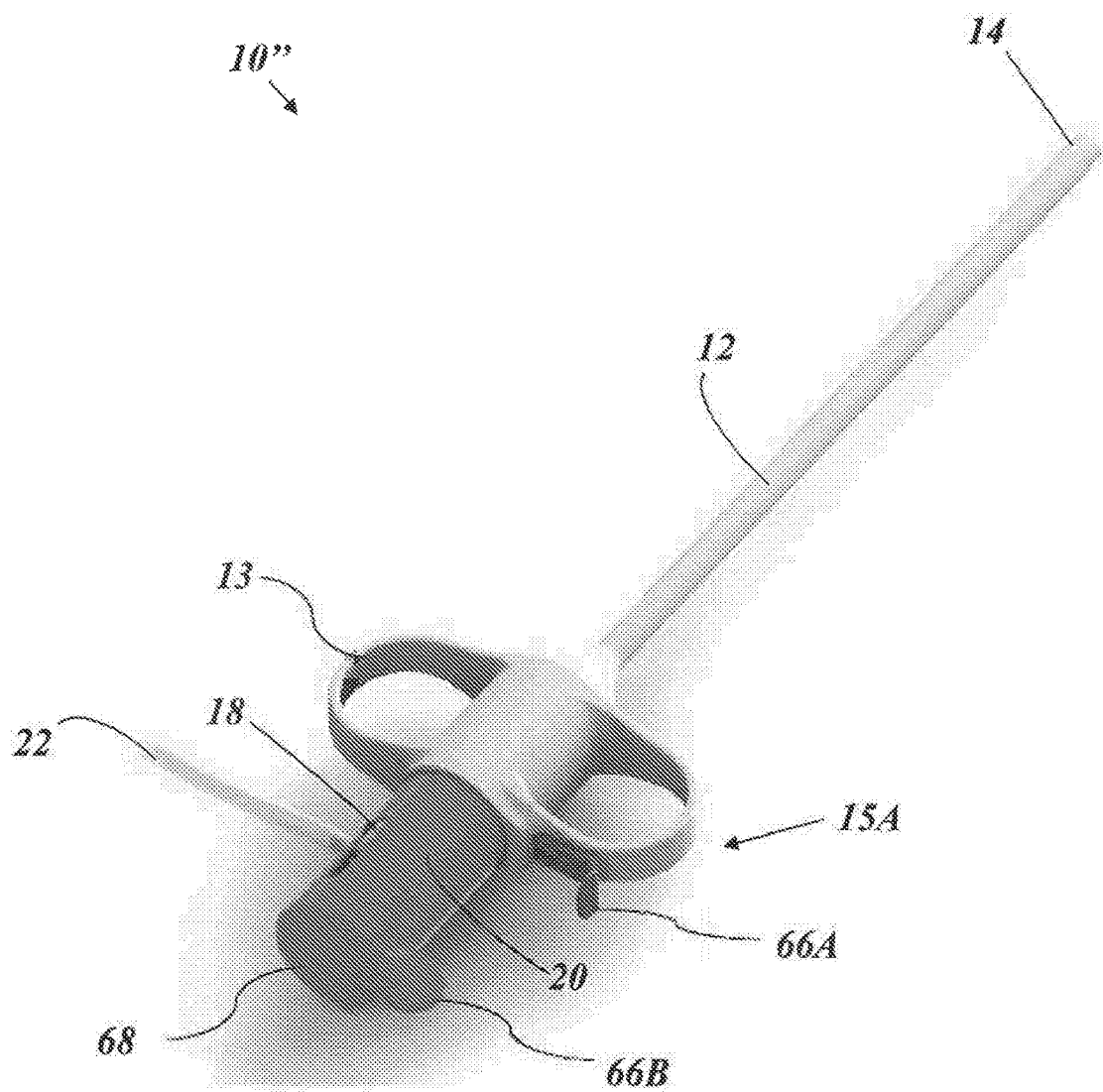
FIG. 26 is a perspective views of another anchor delivery system according to an embodiment of the present invention.

FIG. 26 depicts another anchor delivery system 10" having essentially the same components compared to the anchor delivery systems 10 in FIG. 1 and the anchor delivery system 10' in FIG. 20A. This anchor delivery system 10" has a slightly varied design. The anchor delivery system 10" has a delivery conduit 12, gripper section 13 of the delivery conduit 12, elongate cannula 18, pushrod 20, and supply port 22 having similar functions and interactions as described above. Additionally, the anchor delivery system 10" has a first lock 66A and a second lock 66B. The first lock 66A is at a first end 15A of the delivery conduit 12 for preventing accidental exposure of the tissue piercing tip and aperture 16 before positioning of the anchor delivery system 10". In particular, the first lock 66A can be pushed inward to obstruct an interior lumen of the delivery conduit 12 thus preventing the elongate cannula 18 from being able to slide along towards the delivery aperture 14 of the delivery conduit 12. When the first lock 66A is pulled outward, it unlocks the first lock 66A allowing for the elongate cannula 18 to be able to slide within the delivery conduit 12. The second lock 66B is at the top of the pushrod 20 for preventing accidental delivery or deployment of an anchor 24 prior to inserting of the elongate cannula 18. This second lock 66B is in line or parallel with the gripper section 13 as shown in FIG. 26, when in a locked position. In the locked position, the second lock 66B prevents the pushrod 20 from being able to slide in the elongate cannula 18.

However, when the second lock 66B is rotated clockwise or counter clockwise such that the second lock 66B is no longer parallel with the gripper section, the second lock 66B is unlocked allowing for the pushrod 20 to slide within and along the interior lumen of the elongate cannula 18 to deploy/insert an anchor 24. The pushrod 20 has a thumb pad 68 for ease of use for a user pushing on the pushrod 20.

Figure 27:
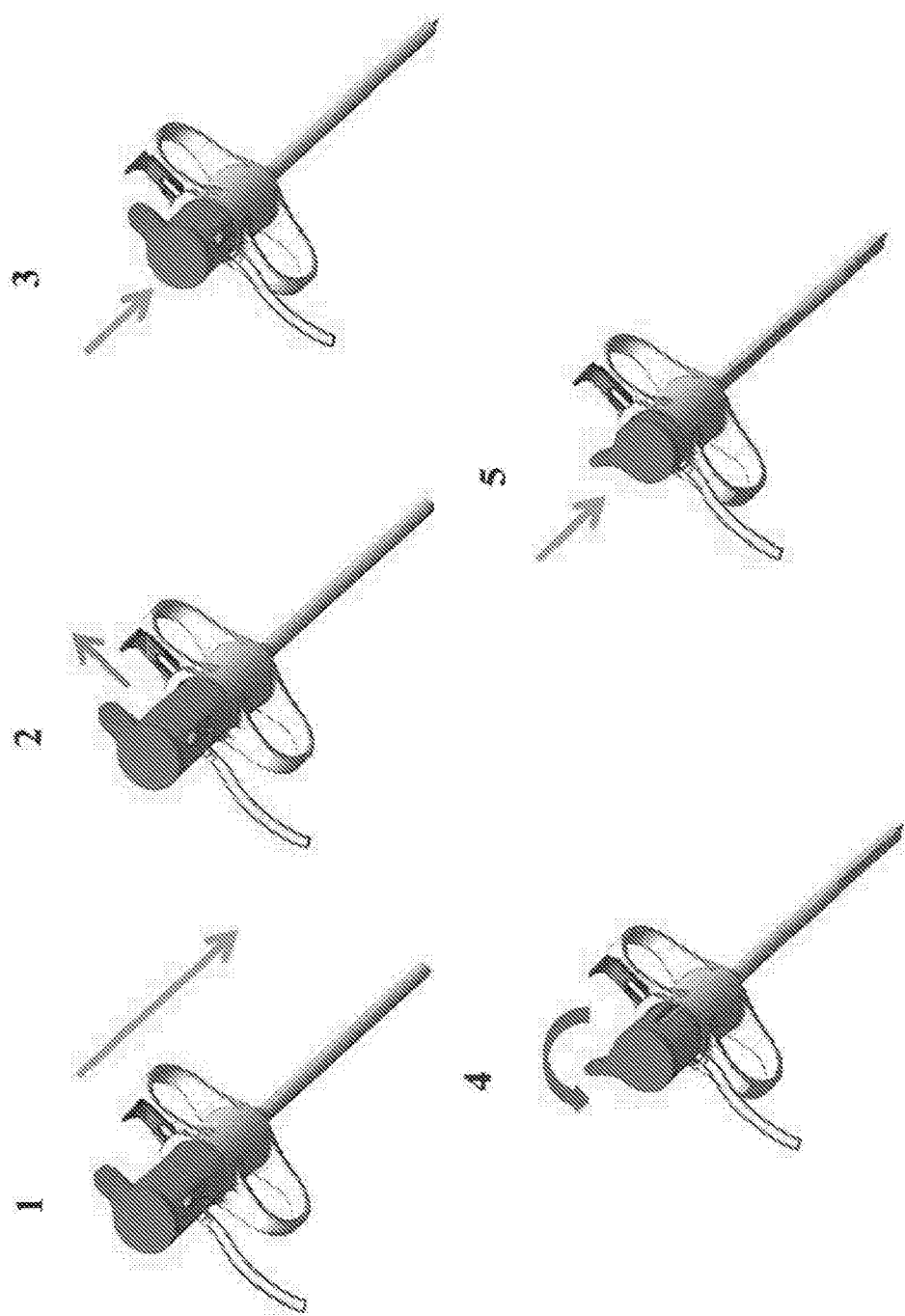
FIG. 27 is perspective views of the operation of the anchor delivery system of FIG. 26 according to one aspect of the present invention.

FIG. 27 depicts the operation of the anchor delivery system 10" of FIG. 26. In particular, the top three drawings illustrate the process of inserting the anchor delivery system 10" into a tissue and the bottom two drawings illustrate the process of deploying the anchor delivery system 10". In step 1, the anchor delivery system 10" is inserted into a vagina for example. In step 2, the first lock 66A is unlocked by a user using their thumb for example to pull out the first lock 66A to an unlocked position. In step 3, a user pushes the elongate cannula 18 such that the tissue piercing tip and aperture 16 is inserted into a tissue. In step 4, the second lock 66B is rotated in either a clockwise or counter clockwise direction to unlock the second lock 66B. In step 5, the pushrod 20 is pushed to deploy an anchor into tissue.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present invention be limited only to the extent required by the appended claims and the applicable rules of law.

It is to be understood that the following claims are to cover all generic and specific features of the invention described herein, and all statements of the scope of the invention which, as a matter of language, might be said to fall therebetween.

What is claimed is:

1. A system for incisionless transvaginal sacrospinous ligament fixation, the system comprising:
   an anchoring unit configured to affix a vaginal wall to a sacrospinous ligament, comprising:
   a collapsible anchor,
   at least one suture having a first end bonded to the anchor and a second end forming a loose tail; and
   at least one locking bead slidable along said loose tail;
   a piercing tip configured to:
   pierce said vaginal wall, and
   partially pierce said sacrospinous ligament to dispose said anchor within said sacrospinous ligament; and
   wherein the at least one locking bead is configured to affix the vaginal wall to the sacrospinous ligament by anchoring the loose tail of the at least one suture to the vaginal wall.

2. The system according to claim 1, wherein said at least one locking bead is configured to be disposed at an apex region of said vaginal wall, thereby affixing said vaginal wall to said sacrospinous ligament.

3. The system according to claim 1, wherein said piercing tip is further configured with a delivery port for delivering a therapeutic substance.

4. The system according to claim 1, further comprising:
   a first arm configured with a first anchor and a first piercing tip; and
   a second arm configured with a second anchor and a second piercing tip, wherein said first arm and said second arm are further configured to grasp a portion of said vaginal wall that is positioned against said sacrospinous ligament, thereby surrounding said sacrospinous ligament.

5. The system according to claim 4, wherein said first piercing tip is configured to deploy said suture through a first piercing of said sacrospinous ligament and said vaginal wall, and wherein said second piercing tip is further configured to deploy said suture through a second piercings of said sacrospinous ligament and said vaginal wall, and wherein said suture is disposed at an apex region of said vaginal wall, thereby affixing said vaginal wall to said sacrospinous ligament.

6. The system according to claim 1, wherein said anchor is configured to rotate and form a T-shape after deployment within the sacrospinous ligament.

7. A method for incisionless transvaginal sacrospinous ligament fixation, the method comprising:
   providing an anchoring unit configured to affix a vaginal wall to a sacrospinous ligament, including:
   a collapsible anchor,
   at least one suture having a first end bonded to the anchor and a second end forming a loose tail; and
   at least one locking bead slidable along said loose tail,
   using a piercing tip, piercing a vaginal wall and partially piercing a sacrospinous ligament;
   disposing the anchor within said partially pierced sacrospinous ligament; and
   sliding the at least one locking bead along said loose tail and affixing the vaginal wall to the sacrospinous ligament by anchoring the loose tail of the at least one suture to the vaginal wall.

8. The method according to claim 7, wherein affixing said vaginal wall to said sacrospinous ligament comprises affixing said vaginal wall to said sacrospinous ligament at an apex region of said vaginal wall.

9. The method according to claim 8, further comprising:
   grasping, via a first arm and a second arm, a portion of said vaginal wall that is positioned against said sacrospinous ligament, thereby surrounding said sacrospinous ligament;
   performing said piercing and disposing steps via said first arm, thereby affixing said vaginal wall to said sacrospinous ligament at a first location; and
   performing said piercing and disposing steps via said second arm, thereby affixing said vaginal wall to said sacrospinous ligament at a second location.

10. The method according to claim 9, wherein disposing comprises disposing the suture at said first and said second locations, and at an apex region of said vaginal wall, thereby affixing said vaginal wall to said sacrospinous ligament.

11. The method according to claim 7, further comprising delivering a therapeutic substance.

* * * * *